US008420308B2

(12) United States Patent
Ben-Shachar et al.

(10) Patent No.: US 8,420,308 B2
(45) Date of Patent: *Apr. 16, 2013

(54) METHODS AND KITS FOR DIAGNOSIS OF SCHIZOPHRENIA

(75) Inventors: Dorit Ben-Shachar, Kiryat Shmuel (IL); Ehud Klein, Timrat (IL)

(73) Assignee: Technion R&D Foundation Ltd., Haifa (IL)

( * ) Notice: Subject to any disclaimer, the term of this patent is extended or adjusted under 35 U.S.C. 154(b) by 595 days.

This patent is subject to a terminal disclaimer.

(21) Appl. No.: 12/258,512

(22) Filed: Oct. 27, 2008

(65) Prior Publication Data

US 2009/0162854 A1    Jun. 25, 2009

Related U.S. Application Data

(63) Continuation-in-part of application No. 10/432,354, filed as application No. PCT/IL01/01106 on Nov. 29, 2001, now Pat. No. 7,442, 496.

(60) Provisional application No. 60/253,927, filed on Nov. 30, 2000.

(51) Int. Cl.
*C12Q 1/00* (2006.01)
*C12Q 1/26* (2006.01)

(52) U.S. Cl.
USPC .................................. 435/4; 435/25; 435/29

(58) Field of Classification Search .................. None
See application file for complete search history.

(56) References Cited

U.S. PATENT DOCUMENTS 7,442,496 B2 * 10/2008 Ben-Shachar et al. ............ 435/4

OTHER PUBLICATIONS

Elkashef et al., Prog. Neuro-Psychopharmacol. Biol. Psych., vol. 26, 2002, pp. 145-148.*
Wu EQ, Birnbaum HG, Shi L, Ball DE, Kessler RC, Moulis M, Aggarwal J, "The Economic Burden of Schizophrenia in the United States in 2002," J Clin Psychiatry. Sep. 2005;66(9):1122-1129.
Allen NC, et al., "Systematic meta-analyses and field synopsis of genetic association studies in schizophrenia: the SzGene database," Nat Genet. Jul. 2008; 40(7):827-34.
Breier A., Su T. P., Saunders R., Carson R. E., Kolachana B. A., deBartolomeis A., Weinberger D. R., Weisenfeld N., Malhotra A. K., Eckelman W. C. and Pickar D. (1997) "Schizophrenia is associated with elevated amphetamine-induced synaptic dopamine concentrations: Evidence from a novel positron emission tomography method," Proc. Natl. Acad. Sci. USA 94, 2569-2574.
Laruelle M., Abi-Dargham A, Gil R., Kegeles L. and Innis R. (1999) "Increased dopamine transmission in schizophrenia: Relationship to illness phase," Biol. Psych. 46, 56-72.
Brenner-Lavie H., Klein E, Zuk R, Gazawi H, Ljubuncic P, Ben-Shachar D, (2008) "Dopamine modulates mitochondrial function in viable SH-SY5Y cells possibly via its interaction with complex I:

Relevance to dopamine pathology in schizophrenia," 1777 (2) 173-185.
Ben-Shachar D, Zuk R, Gazawi H, Ljubuncic P. (2004) "Dopamine toxicity involves mitochondrial complex I inhibition: implications to dopamine related neuropsychiatric disorders," Biochemical Pharmacol. 67, 1965-1974.
Aganova E. A., et al. "Morphometric Analysis of Synaptic Contacts in the Anterior Limbic Cortex in the Endogenous Psychoses" UDC 616.895.58-07:616,831.314-0918, 1992 Plenum Publishing Corporation.
Barbeau David, et al. "Decreased Expression of the Embryonic Form of the Neural Cell Adhesion Molecule in Schizophrenic Brains" Proc. Natl. Acad. Sci, vol. 92, pp. 2785-2789, Mar. 1995.
Beal Flint M, "Does Impairment of Energy Metabolism Result in Excitotoxic Neuronal Death Inneurodegenerative Illnesses?" 1992 American Neurological Association.
Ben-Shachar Dorit, et al. "Increased Mitochondrial Complex I Activity in Platelets of Schizophrenic Patients" International Journal of Neuropsychopharmacology (1992), 2, 245-253.
Ben-Shachar Dorit, et al. "Dopamine Neurotoxicity: Inhibition of Mitochondrial Respiration" Journal of Neurochemistry, Raven Press Ltd, New York 1995, International Society for Neurochemistry.
Bromet Evelyn et al. "Basic Principles of Epidemiologic Research in Schizophrenia" Handbook of Schizophrenia, vol. 3: Nosology, Epidemiology and Genetics, 1988.
Burkhardt Carolyn, et al. "Neuroleptic Medications Inhibit Complex I of the Electron Transport Chain". 1993 American neurological Association, Annals of Neurology, vol. 33, No. 5, pp. 512-517.
Cavelier Lucia, et al. "Decreased Cytochrome-C Oxidase Activity and Lack of Age-Related Accumulation of Mitochondrial DNA Deletions in the Brains of Schizophrenics" 1995 Academic Press, Inc, Genomics 29, 217-224 (1995).
Cohen Gerald, et al "Parkinson Disease: A New Link Between Monoamine Oxidase and Mitochondrial Electron Flow" Proc. Natl. Acad. Sci. vol. 94 pp. 4890-4894, May 1997, Biochemistry.
Davis Kenneth L., "Dopamine in Schizophrenia: A Review and Reconceptualization" Am J Psychiatry 148:11, 1991.
Da Prada M, et al. "Platelets as a Model for Neurones?" Experientia 44 (1988) , pp. 115-126.
Docherty, Nancy M. PhD et al, "Communication Disturbances in Schizophrenia and Mania", Arch Gen Psychiatry, 1996;53:358-364.
Dror, N., et al, "State-Dependent Alterations in Mitochondrial Complex I Activity in Platelets: A Potential Peripheral Marker for Schizophrenia", Molecular Psychiatry (2002) 7, 995-1001 Nature Publishing Group.
Estornell Ernesto et al. "Assay Conditions for the Mitochondrial NADH: Coenzyme Q Oxidoreductase" Federation of European Biochemical Societies vol. 332. No. 1,2, 127-131, 1993.
Ganguli Rohan, et al, "Autoimmunity in Schizophrenia: A Review O Frecent Findings" Annals of Medicine 25: 489-496, 1993.
Gavin Claire E. et al. "Manganese and Clacium Efflux Kinetics in Brain Mitochondria" Biochem J. (1990) 226, 329-334 vol. 266.

(Continued)

*Primary Examiner* — Jeffrey Stucker
*Assistant Examiner* — Stephen Gucker
(74) *Attorney, Agent, or Firm* — Pearl Cohen Zedek Latzer, LLP; Zeev Pearl

(57) ABSTRACT

The present invention provides methods and kits for the diagnosis of schizophrenia, which employ mitochondrial complex I as a peripheral biological marker for schizophrenia. In an embodiment of the invention, the present invention provides a method for diagnosing schizophrenia in a subject by determining the level of m-RNA or protein mitochondrial complex I subunits and its activity by determining the cellular basal respiration through complex I enzyme.

13 Claims, 5 Drawing Sheets

OTHER PUBLICATIONS

Gur Rachel E. et al. "Regional Brain Function in Schizophrenia" Arch Gen Psychiatry, vol. 44, Feb. 1987:44:126-129.

Harlow ED, et al. "Antibodies—A Laboratory Manual" Cold Spring Harbor Laboratory 1988.

Hatefi Y "Introduction—Preparation and Properties of the Enzymes and Enzyme Complexes of the Mitochondrial Oxidative Phosphorylation System" vol. 53, 1978, pp. 3-4, Biomembranes—Part D: Biological Oxidations.

Hietala Jarmo et al. "Dopamine in Schizophrenia" Annals of Medicine 28: 557-561m 1996, The Finnish Medical Society.

Holcomb Henry H et al., "Functional Sites of Neuroleptic Drug Action in the Human Brain; PET/FDG Studies With and Without Haloperidol" Am J Psychiatry 153: Jan. 1, 1996.

Kaiya H. et al., "Second Messenger Imbalance Hypothesis of Schizophrenia" Prostaglandins Leukotienes and Essential Fatty Acids (1992) 46, 33-38.

Masterson Winifred, "Glucose/Mitochondria in Neurological Conditions" Glucose Metabolism in the Brain eds. Donard S. Dwyer, International Reviews of Neurobiology vol. 51, American Press, 2002, pp. 325-376.

Meltzer H.Y. et al. "Clinical Services Research" Schizophrenia Bulletin, vol. 18, No. 4, 1992, pp. 614-625.

Krige David, et al. "Platelet Mitochondrial Function in Parkinson's Disease" American Neurological Association, 1992;32:782-788.

Kung Lili et al. "Mitochondiral Pathology in Human Schizophrenic Striatum: A Postmortem Ultrastuctural Studay" Synapse 31:67-75 (1999) Wilely-Liss, Inc.

McCormack James G. et al. "Influence of Calcium Ions on Mammalian Intramitochondrial Dehydrogenases" Methods in Enzymology, vol. 174 1989 Academic Press, Inc, pp. 95-118.

McGlashan Thomas H. "A Selective Review of Recent North American Long-Term Followup Studies of Schizophrenia" vol. 14, No. 4, 1988, Schizophrenia Bulletin, pp. 515-542.

McGlashan Thomas H. et al. "The Positive-Negative Distinciton in Schizophrenia" Arch Gen Psychiatry—vol. 49, Jan. 1992, pp. 63-72.

Moilanen, Kristiina et al, "Reasons for the Diagnostic Discordance Between Clinicians and Researchers in Schizophrenia in the Northern Finland 1966 Birth Cohort", Soc Psychiatry Psychiatr Epidemiol (2003) 38:305-310.

Parker William Davis Jr. et al. "Cytochrome Oxidase Deficiency in Alzheimer's Disease" Neurology 40, Aug. 1990; 40:1302-1303.

Pletscher A., "Platelets as Models: Use and Limitations", Experientia 44 (1988), Birkhauser Verlag,, CH-4031 Basel (Switzerland), pp. 152-155.

Prince Jonathan A. et al., "Mitochondrial Function is Differentially Altered in the Basal Ganglia of Chronic Schizophrenics" Neuropsychopharmacology 1999, vol. 21, No. 3, pp. 372-379.

Przedborski Serge et al., "Chronic Levodopa Administration Alters Cerebral Mitochondrial Respiratory Chain Activity" American Neurological Association 1993;34:715-723.

Raedler, et al. "Schizophrenia as a Developmental Disorder of the Cerebral Cortex", Current Opinion in Neurobiology 1998, 8:157-161.

Ragan C.I. et. al, "Sub-Fractionation of Mitochondria and Isolation of the Proteins of Oxidative Phosphorylation," In "Mitochondria: A Practical Approach." (V.M. Darley-Usmar, D. Rickwood and M. T. Wilson, eds.) pp. 79-112. IRL Press, Oxford.

Rosenthal, Robert E. et. al, "Cerebral Ischemia and Reperfusion: Prevention of Brain Mitochondrial Injury by Lodoflazine", Journal of Cerebral Blood Flow and Metabolism 7:752-758, 1987 Raven Press, Ltd., New York.

Schapira, A.H.V. et al., "Mitochondrial Complex I Deficiency in Parkinson's Disease", Journal of Neurochemistry, Raven Press, Ltd. New York, 1990 International Society for Neurochemistry, vol. 54, Issue 3, pp. 823-827, Mar. 1990.

Seeman, Philip, "Dopamine Receptors and the Dopamine Hypothesis of Schizophrenia", Synapse 1:133-152 (1987), Alan R Liss, Inc.

Tamminga, Carol A. MD, PhD; et. al., "Limbic System Abnormalities Identified in Schizophrenia Using Positron Emission Tomography With Fluorodeoxyglucose and Neocortical Alternations With Deficit Syndrome", Arch Gen Psychiatry—vol. 49, Jul. 1992, pp. 522-530.

Sheitman, Brian et al, "The Evaluation and Treatment of First-Episode Psychosis". Dorothea Dix Hosp, CRU-Edgerton Bldg, 809 Ruggles Dr., Raleigh, NC.

Singer, Thomas P. "Determination of the Activity of Succinate, NADH, Choline, and A-Glycerophosphate Dehydrogenases", Dept. of Biochem and Biophys, Univ. of Cal, San Francisco & Molecular Biol. Div. Veterans Adm. Hosp, San Fran. California, Methods Biochem Anal. 1974;22:123-75.

Storrie, Brian and Madden, Edward A. "Isolation of Subcellular Organelles", Methods of Enzymology, vol. 182, copyright 1990 by Academic Press.

Strunecká, A., and Řípová, D, Review "What Can the Investigation of Phosphoinositide Signaling System in Platelets of Schizophrenic Patients Tell Us?" Prostaglandins, Leukotrienes and Essential Fatty Acids (1999)61(1), 1-5 Harcourt Publishers Ltd.

Takahashi, Yasuo, "An Enzymological Study on Brain Tissue of Schizophrenic Patients*. Carbohydrate Metabolism. Part I. Glucose", Folia Psychiatrica et Neurologica, Japonica vol. 7, No. 3, 1953.

Tsuange, Ming T. MD, "Toward Reformulating the Diagnosis of Schizophrenia", Am J. Psychiatry 157:1041-1050, Jul. 2000.

Tsuange, Ming T. MD, PhD, "Suicide in Schizophrenics, Manics, Depressives, and Surgical Controls", Arch Gen Psychiatry—vol. 35, Feb. 1978, pp. 153-155.

Wesley Dingman C. et al. "Discriminating Characteristics of Suicides" Acta Psychiatr. Scand. 1986:74:91-97.

Whatley, S.A. et al. "Mitochondrial Involvement in Schizophrenia and Other Functional Psychoses", Neurochemical Research, vol. 21, No. 9, 1996, pp. 995-1004, Plenum Publishing Corp.

Whatley, SA et al, "Superoxide, Neuroleptics and the Ubiquinone and Cytochrome B5 Reductases in Brain and Lymphocytes From Normals and Schizophrenic Patients", Molecular Psychiatry (1998) 3, 227-237 Stockton Press.

Wyatt, R.J. et al, "An Economic Evaluation of Schizophrenia—1991", Soc Psychiatry Psychiatr Epidemiol (1995) 30:196-205, Springer-Verlag.

Yao, J.K. and Van Kammen, D.P., "Incorporation of 3H-Arachidonic Acid Into Platelet Phospholipids of Patients With Schizophrenia", Prostaglandins, Leukotrienes and Essential Fatty Acids (1996) 55(1&2),21-26, Pearson Professional Ltd.

Sheitman, Brian et al, "The Evaluation and Treatment of First-Episode Psychosis". Dorothea Dix Hosp, CRU—Edgerton Bldg, 809 Ruggles Dr., Raleigh, NC., Schizophrenia Bulletin, vol. 23(4), 1997, 653-661.

Hatefi Youssef "Preparation and Properties of NADH: Cytochrome c Oxidoreductase (Complex I-III)," vol. 53, 1978, pp. 5-10, Biomembranes—Part D: Biological Oxidations.

* cited by examiner

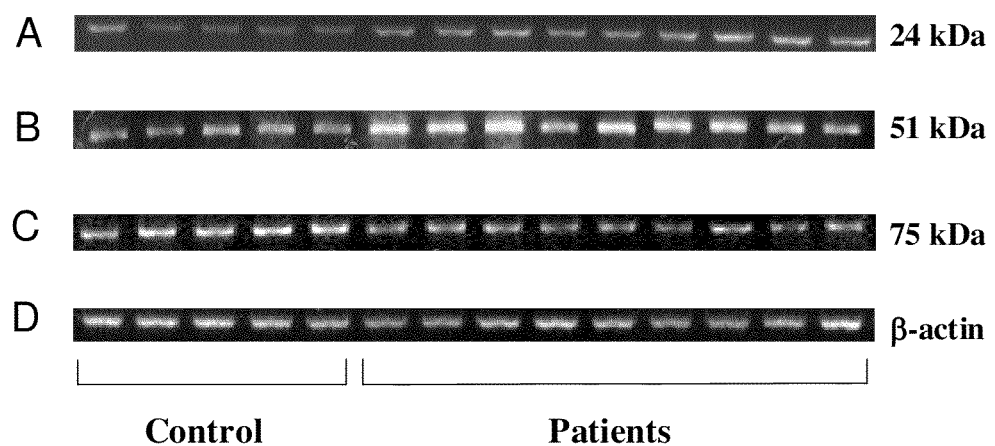
Figure 3A-D
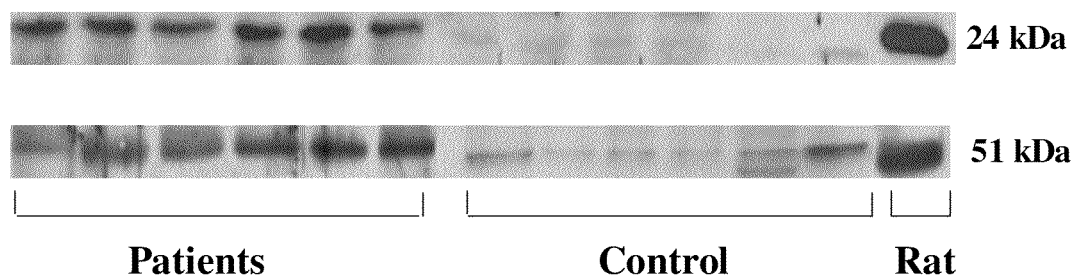
Figure 4

METHODS AND KITS FOR DIAGNOSIS OF SCHIZOPHRENIA

CROSS REFERENCE TO RELATED APPLICATIONS

This application is a Continuation-in-Part of U.S. patent application Ser. No. 10/432,354, now U.S. Pat. No. 7,442, 496, filed May 29, 2003, which is a National Phase Application of International Patent Application No. PCT/IL01/01106, filed on Nov. 29, 2001, which claims priority of U.S. Provisional Application Ser. No. 60/253,927, filed Nov. 30, 2000, all of which are hereby incorporated in their entirely by reference.

FIELD OF THE INVENTION

The present invention generally relates to the field of disease diagnostics. More specifically, the present invention relates to a method for the diagnosis of schizophrenia.

BACKGROUND OF THE INVENTION

Schizophrenia is the most disabling psychiatric disorder, with a lifetime prevalence of about one-percent in the population (Bromet et al, 1974). Because schizophrenia usually appears early in life and is often chronic, the costs of the disorder are substantial. The disorder appears to be uniformly distributed worldwide, although pockets of high or low prevalence may exist (Docherty et al., 1996). Unemployment rates can reach 70%-80% in severe cases, and it is estimated that schizophrenic patients constitute 10% of the totally and permanently disabled. Homelessness and schizophrenia have been linked; it has been estimated that about one-third of homeless single adults suffer from severe mental illness, largely schizophrenia.

The essential features of schizophrenia consist of a mixture of characteristic signs and symptoms that have been present for a significant length of time during a 1-month period with some signs of the disorder persisting for at least 6 months (According to Diagnostic and Statistical Manual of Mental Disorder-IV, hereinafter DSM-IV). The symptoms involve multiple psychological processes, such as perception (hallucinations), ideation, reality testing (delusions), thought processes (loose associations) feeling (flatness, inappropriate affect), behavior (catatonia, disorganization), attention, concentration, motivation (avolition, impaired intention and planning) and judgment. No single symptom is pathognomonic of schizophrenia. These psychological and behavioral characteristics are associated with a variety of impairments in occupational and social functioning. The disorder is noted for great heterogeneity across individuals and variability within individuals over time. It is also associated with an increased incidence of suicide, which occurs in up to 10% of patients (Dinagman et al. 1986; Tsuang, 1978; McGlasban, 1988).

The characteristic symptoms of schizophrenia have often been conceptualized as falling into two broad categories—positive and negative (or deficit) symptoms—with a third category, disorganized, recently added. The positive symptoms include delusions and hallucinations. Disorganized symptoms include disorganized speech (Docherty et al., 1996), disorganized behavior and poor attention. Negative symptoms include restricted range and intensity of emotional expression (affective flattening), reduced thought and speech productivity (alogia), anhedonia, and decreased initiation of coal-directed behavior (avolition) (McGlashan et al, 1992).

According to DSM-IV, subtypes of schizophrenia are defined by the predominant symptoms at the time of the most recent evaluation and therefore may change over time. These subtypes include 1) paranoid type, in which preoccupation with delusions or auditory hallucinations is prominent; 2) disorganized type, in which disorganized speech and behavior and flat or inappropriate affect are prominent; 3) catatonic type, in which the characteristic motor symptoms are prominent; 4) undifferentiated type, which is a nonspecific category used when none of the other subtype features is prominent; and 5) residual type, in which there is an absence of prominent positive symptoms but continuing evidence of disturbance (e.g., negative symptoms or positive symptoms in an attenuated form) (Barbeau et al, 1995).

The etiology of schizophrenia is still unknown. Recent advances in neuroscience and psychopharmacology have suggested a wide array of competing mechanisms that may be involved in schizophrenia, including a deficit in one or more neurotransmitters (e.g., dopamine, serotonin, GABA and glutamate), their second messengers (Kaiya, 1992; Yao et al., 1996; Strunecka et al. 1999), neurodevelopmental defects in brain (Raedler et al., 1998), autoimmune mechanisms (Ganguli et al. 1993) and potential genetic risk factors (Allen et al. 2008). Dopamine involvement in schizophrenia is still attracting considerable attention despite the lack of direct evidence for abnormal dopaminergic function in the disorder. This is primarily based on the high correlation between the therapeutic efficacy of antipsychotic drugs and their potency as dopamine receptors blockers (Seeman, 1987), and the ability of dopamine agonists (such as bromocriptine and L-DOPA) to induce acute psychotic symptoms with marked resemblance to schizophrenia. It has been suggested that acute psychotic episodes are associated with a hyperdopaminergic state in the mesolimbic regions, while negative symptoms are associated with a hypodopaminergic state in the mesocortical projections to the frontal cortex (Davis et al., 1991). More recent, direct evidence for dopamine hyperactivity has emerged from imaging studies implicating dysfunction in dopamine metabolism, storage, release or uptake mechanisms in dopamine meso-limbic systems in schizophrenia (Breier A., et al., 1997. Laruelle et al., 1999).

Symptoms of other mental disorders, especially depression but also obsessive and compulsive symptoms, somatic concerns, dissociative symptoms and other mood or anxiety symptoms, are frequently seen with schizophrenia. The heterogeneity of the disorder and its comorbidity with symptoms of other mental disorders frequently renders schizophrenia difficult to diagnose. At present, definitive diagnosis of schizophrenia depends on descriptive behavioral and symptomatic information. Further, a very long time period, approximately 6 months, is required for the diagnosis of schizophrenia.

Since there is neither an effective biological marker for identifying schizophrenia (Willner, 1997; Hietala, et al., 1996), nor an accurate and rapid diagnosis for more optimal management of the disease at its different stages (Sheitman et al., 197) there remains an essential need for a reliable biological assay for the diagnosis and follow-up of schizophrenia. Identifying a peripheral biological marker will provide a) a more precise diagnosis and prognosis and might even shorten the 6-month period needed for diagnosis of schizophrenia; b) the possibility of using the peripheral marker as an objective tool for the patient's compliance to medication, if the marker responds differently in the presence of different types of antipsychotic drugs; and c) a correlation between the candidate marker and any feature of schizophrenia will contribute to the knowledge of the basic pathophysiology of the disorder, which might lead to new therapeutic strategies more specific and with fewer side effects.

SUMMARY OF THE INVENTION

The present invention provides a method for diagnosing schizophrenia in a subject, the method comprising the steps of: obtaining a sample from the subject, determining the level of one or more mitochondrial complex I subunits protein or mRNA encoding thereof in the sample; and comparing the level of each mitochondrial complex I subunit protein or mRNA encoding thereof of the sample with a normative value of mitochondrial complex I subunit protein or mRNA encoding thereof; wherein an altered level of at least one mitochondrial complex I subunit mRNA or protein encoding thereof in the sample is indicative of the subject having schizophrenia.

In an embodiment of the invention, the sample used for diagnosing schizophrenia in this invention is a blood sample, wherein the blood sample is a platelet, lymphocyte, leukocyte, monocyte, T-cell, B-cell, neutrophil, EBV transformed lymphocytes or immortal blood cells sample.

In an embodiment of the invention, the level of m-RNA of mitochondrial complex I is determined by measuring the level of m-RNA of a subunit of mitochondrial complex I. In another embodiment, the level of protein of mitochondrial complex I is determined by measuring the level of protein of a subunit of mitochondrial complex I.

In an embodiment of the invention, a higher level of m-RNA or protein of the subunit of mitochondrial complex I in the sample from the subject compared with the normative value is indicative of the subject having schizophrenia.

In an embodiment of the invention, the mitochondrial complex I protein subunit is a 24 kDa subunit. In another embodiment, the mitochondrial complex I protein subunit is a 51 kDa subunit. In another embodiment the mitochondrial complex I protein subunit is a 75 kDa subunit.

In an embodiment of the invention the level of m-NA of the subunit of mitochondrial complex I is determined by isolating RNA from the sample, contacting the RNA with primers which are specific for the subunit of mitochondrial complex is performing real time quantitative-PCR on the sample, and determining the level of m-RNA of the subunit of mitochondrial complex I.

In an embodiment of the invention, the binding protein is an antibody. The antibody is a polyclonal antibody, a monoclonal antibody or a recombinant antibody. In an embodiment of the invention the binding protein is labeled with a detectable label, which can be an enzyme, a fluorophore, a chromophore, a radioisotope a dye, a bioluminescent agent or a chemiluminescent agent.

In an embodiment of the invention, this invention provides a method for diagnosing schizophrenia in a subject, the method comprising the steps of obtaining a sample from the subject; determining the cellular basal respiration through complex I enzyme; adding an inhibitor to the sample and determining the inhibition of the cellular respiration through complex I, wherein a decrease in respiration and/or an increase in inhibition of cell respiration through complex I enzyme as compared to cell respiration and its inhibitory values through complex I in a normative person is indicative to schizophrenic patients.

In an embodiment of the invention, this invention provides a method for diagnosing schizophrenia in a subject the method comprising the steps of: obtaining a sample from the subject; determining the cellular basal respiration through complex I enzyme; adding an inhibitor to the sample and determining the inhibition of the cellular respiration through complex I, wherein a decrease in respiration by at least 30% and/or an increase in inhibition of cell respiration through complex I enzyme by more than 1.5 folds as compared to cell respiration and its inhibitory values through complex I in a normative person is indicative to schizophrenic patients.

BRIEF DESCRIPTION OF THE DRAWINGS

The present invention will be understood and appreciated more fully from the following detailed description taken in conjunction with the appended drawings in which:

FIG. 3A-D: presents a photograph depicting RT-PCR analysis of mitochondiral complex I subunits from platelets of schizophrenic patients and healthy control subjects FIG. 3A shows m-RNA levels of the 24 kDa subunit of complex I FIG. 3B shows m-R-NA levels of the 51 kDa subunit of complex a FIG. 3C shows m-RNA levels of the 75 kDa subunit of complex I; and FIG. 3D shows m-RNA levels of beta actin.

FIG. 4: presents a photograph of ECL western blot analysis of the 24 and 51 kDa subunits of mitochondrial complex I in platelets of schizophrenic patients and healthy control subjects, Rat brain mitochondria are used as a positive control.

FIG. 6: depicts the levels of respiration through the different enzymatic complexes of the respiratory chain in the presence or absence of dopanmine.

DETAILED DESCRIPTION OF THE INVENTION

Figure 1:
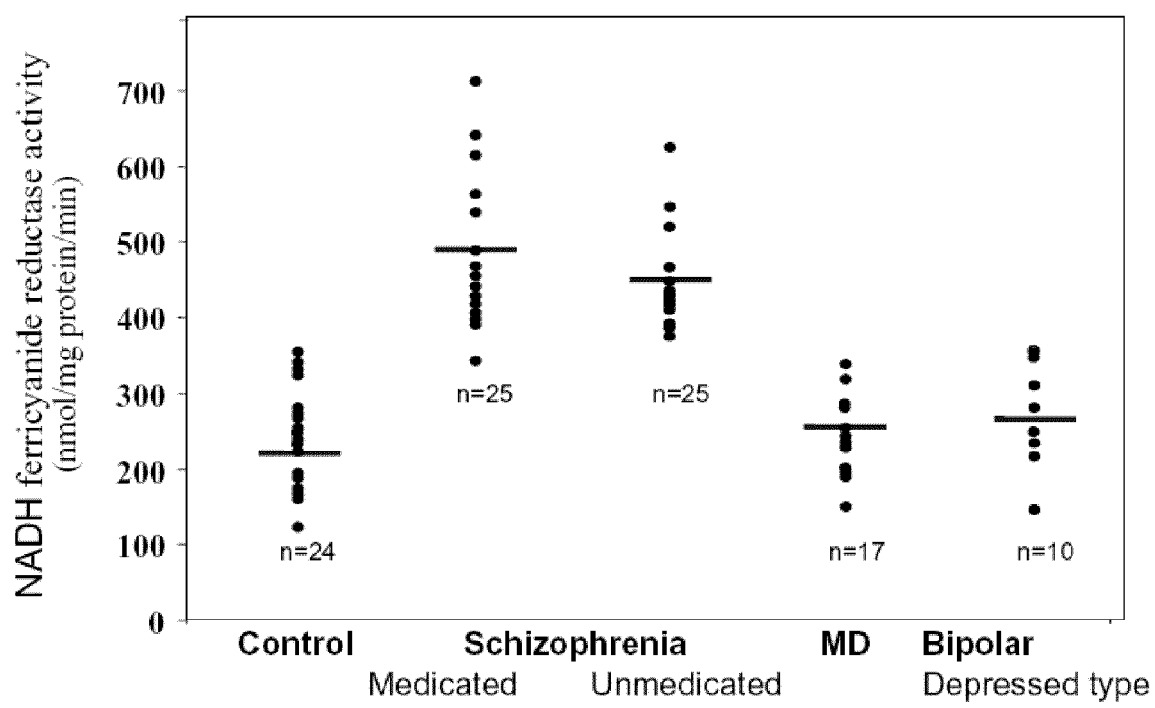
FIG. 1: depicts individual values of NADH ferricyanide reductase activity in medicated (MS) and unmedicated (US) schizophrenic patients, patients with major depression (MD), patients with bipolar disorder (BP), and control subjects (C).

The present invention provides methods and kits for the diagnosis of schizophrenia which employ mitochondrial complex I as a peripheral biological marker for schizophrenia. The identification of mitochondrial complex I as a biological marker provides several advantages such as 1) a reliable and rapid biological assay for the diagnosis and follow-up of schizophrenia that may also shorten the 6-month period currently needed for the diagnosis of schizophrenia, 2) contributes to the knowledge of the basic pathophysiology of the disease, which might lead to new therapeutic strategies, and 3) permits the mitochondrial complex I to be a target Gene for this multi-gene disorder.

As demonstrated herein, mitochondrial complex I activity is significantly altered in platelets of schizophrenic patients compared with control subjects. Patients with affective disorders such as major depression and bipolar disorder, by contrast, show a similar mitochondrial complex I activity as control subjects. Further, the levels of m-RNA and protein of mitochondrial complex I are significantly altered in platelets or lymphocytes of schizophrenic patients compared with control subjects. Thus, the present invention provides methods and kits for diagnosing schizophrenia by determining the level of activity of a mitochondrial complex I enzyme in a subject and comparing the activity with a normative value of activity of the mitochondrial complex I enzyme. The present invention further provides methods and kits for diagnosing schizophrenia by determining the level of m-RNA or protein of complex I submits in a subject and comparing the level of m-RNA or protein with a normative level of m-RNA or protein of mitochondrial complex I subunits.

In an embodiment of the invention, this invention provides a method for diagnosing schizophrenia in a subject, the method comprising the steps of: obtaining a sample from the subject; determining the level of one or more mitochondrial complex I subunits protein or mRNA encoding thereof in the sample; and comparing the level of each mitochondrial complex I subunit protein or mRNA encoding thereof of the sample with a normative value of mitochondrial complex I subunit protein or mRNA encoding thereof, wherein an altered level of at least one mitochondrial complex I subunit mRNA or protein encoding thereof in the sample is indicative of the subject having schizophrenia.

In an embodiment of the invention, the level of mitochondrial complex I subunit protein or m-RNA encoding thereof is higher in a schizophrenic subject by mean of at least 1.5 folds compared with normative value. In an embodiment of the invention, the level of mitochondrial complex I subunit protein or mRNA encoding thereof is higher in a schizophrenic subject by mean of at least 2.5 folds compared with normative value. In an embodiment of the invention, the level of mitochondrial complex I subunit protein or mRNA encoding thereof is higher in a schizophrenic subject by mean of at least 3.5 folds compared with normative value. In an embodiment of the invention, the level of mitochondrial complex I subunit protein or mRNA encoding thereof is higher in a schizophrenic subject by between 1.5-10 folds compared with normative value. In an embodiment of the invention, the level of mitochondrial complex f subunit protein or mRNA encoding thereof is higher in a schizophrenic subject by between 0.5-4 folds compared with normative value.

In an embodiment of the invention, the sample used for diagnosing schizophrenia in this invention is a blood sample, wherein the blood sample is a platelet, lymphocyte, leukocyte, monocyte, T-cell, B-cell, neutrophil, EBV transformed lymphocytes or immortal blood cells sample.

In another embodiment of the invention, this invention provides methods of diagnosing schizophrenia by determining the level of protein or mRNA of complex I subunits and its activity. In another embodiment, the mRNA subunits and the corresponding protein subunits of complex I enzyme refer to any of the 45 different genes and their corresponding proteins. Non limiting examples of mRNA subunits include NDUIFAB1, NDUFS1, NDUFS2, NDUFS3, NDUFS4, NDUFS7, NDUFS8, NDUFV1 and NDUFV2. Non limiting examples of protein subunits include 51 kD, 24 kD, 75 kD, 18 kD, 19 kD and 21 kD subunits.

In an embodiment of the invention, a reagent is used for determining the n-RNA level of a subunit of mitochondrial complex I. The reagent comprises at least one reagent and buffer for isolating RNA from the sample. In another embodiment, the reagent comprises at least two primers which are specific for the subunit of mitochondrial complex I. In another embodiment reagents and buffers are used for a real time quantitative-PCR assay.

In an embodiment of the invention, the reagent is for determining the protein level of a subunit of mitochondrial complex I. The reagent comprises a binding protein, which specifically binds to the subunit of mitochondrial complex I. In an embodiment of the invention, the level of protein of the subunit of mitochondrial complex I is determined by contacting the sample with a binding protein which specifically binds to the subunit of mitochondrial complex I, and determining the amount of binding protein bound to the subunit of mitochondrial complex I. In an embodiment of the invention, the binding protein is an antibody. The antibody is a polyclonal antibody, a monoclonal antibody or a recombinant antibody. In an embodiment of the invention, the binding protein is labeled with a detectable label. The label is an enzyme, a fluorophore, a chromophore, a radioisotope, a dye, a bioluminescent agent or a chemiluminescent agent.

For the purposes of this invention, schizophrenic patients are broadly categorized as a function of their clinical state as being in an acute phase or in a residual (chronic) phase. Patients in acute phase experience acute relapse or are in acute psychotic exacerbation. Patients in residual phase are patients whose condition is stable (chronic). Residual patients are divided into two groups: 1) patients with pronounced positive symptoms (chronic active); and 2) patients without pronounced positive symptoms who experience mainly negative symptoms. Positive symptoms include delusions and hallucinations. Negative symptoms include restricted range and intensity of emotional expression (affective flattening), reduced thought and speech productivity (alogia), anhedonia, and decreased initiation of goal-directed behavior (avolition). For the purpose of this invention, a schizophrenic subject can be in any one of the clinical states defined above.

Applicant has determined that mitochondrial complex I is altered in schizophrenic patients when compared with a normative value of mitochondrial complex I. A "normative value" means a value of a normal mitochondrial complex I level of a control subject who does not have schizophrenia.

In an embodiment of the invention of the present invention, mitochondrial complex I is assayed by determining the level of activity of a mitochondrial complex I enzyme. Thus, the present invention provides a method for diagnosing schizophrenia in a subject by determining the level of activity of a mitochondrial complex I enzyme in a sample obtained from the subject, and comparing the level of activity in the sample with a normative value of mitochondrial complex I enzyme activity. An altered level activity of mitochondrial complex I enzyme compared with the normative value is indicative of the subject having schizophrenia.

The sample can be any sample that contains mitochondrial complex I for example a tissue sample. Suitable samples may be obtained from a veterinary or human patient and include, but are not limited to, whole blood cells, any mononuclear cell, leukocytes, lymphocytes, T-cells, B-cells, monocytes, platelets, megakaryocytes, neutrophils, eosinophils, basophils or peripheral blood mononuclear cells.

In an embodiment of the invention, the blood sample is enriched for mitochondria. General methods for isolation of mitochondria are disclosed in Ben-Schachar et al (1995), Gavin et al (1990), Rosenthal et al (1987) and McComark and Denton (1989) and described in detail in the examples that follow. The advantage of studying mitochondrial respiration lies in the fact that mitochondria are partly independent organelles, contain their own DNA and are highly preserved along evolution and in different tissues.

In an embodiment of the invention, the blood sample is a blood platelet sample. Platelets have been traditionally used as a peripheral model that may reflect brain changes in several neuropsychiatric disorders. Numerous studies have shown that platelets from schizophrenic patients behave differently than those isolated from healthy controls in dopamine uptake, 5-HT content, arachidonic acid metabolism, inositol phosphate levels and disturbance of calcium homeostasis (Kaiya, 1992 Yao et al., 1996; Strunecka et al. 1999). A correlation between biochemical changes in brain and platelets was also reported. For example, a reduction in imipramine binding was found both in platelets and in postmortem brains of deceased depressed patients and patients who committed suicide (Wirz-Justce, 1988). In patients with Parkinson's or Alzheimer's diseases, a correlation has been demonstrated between platelet and postmortem brains for the reduction in mitochondrial complex I and cytochrome c oxidase activities, respectively (Parker et al. 1990; Schapira et al. 1990). In addition, biochemical and pharmacological similarities exist between blood platelets and 5HT or DA containing neurons of the CNS (Da Prada et al., 1988).

In an embodiment of the invention, the mitochondrial complex I enzyme is a mitochondrial enzyme respiratory chain enzyme. In an embodiment of the invention, the enzyme is NADH dehdrogenase. NADH dehydrogenase activity can be measured using well-known assays, such as the assays described in Singer et al. (1974); Estornell (1993); Hatefi (1978); Ragan et al. (1987), and Ben Schachar et al. (1999). Briefly, NADH dehydrogenase activity is measured using an electron acceptor. In an embodiment of the invention, the electron acceptor is a biological electron acceptor, such as ubiquinone. In another embodiment, the electron acceptor is an artificial electron acceptor, such as ferricyanide, for example potassium ferricyanide. The assay comprises incubating a sample obtained from a subject with NADH and the electron acceptor, and measuring the change in absorbance of NADH at 340 nm over time.

The alteration in the level of activity of the mitochondrial complex I enzyme is dependent on the state of the disease. For example, Applicant has demonstrated a significant increase in mitochondrial complex I activity in mitochondria from platelets of medicated and unmedicated patients at acute exacerbation compared to control subjects, as discussed in detail in the examples below. Furthermore, Applicant has demonstrated a significant increase in mitochondrial complex I activity in mitochondria from platelets of residual patients with positive symptoms compared to control subjects, as discussed in detail in the examples below. On the other hand, Applicant has demonstrated a decrease in mitochondrial complex I activity in mitochondria from platelets of residual patients with negative symptoms compared to control subjects, as discussed in detail in the examples below. No difference in enzyme activity was observed between depressed patients with recurrent major depression or bipolar disorder and control subjects.

Other respiratory chain enzymes of mitochondrial complex I are the succinate dehydrogenase (complex II), cytochrome b-c1 complex (complex III) the cytochrome c oxidase complex (complex IV) and the ATP synthase (complex IV). The level of activity of complexes II, IV and V are not altered in schizophrenic patients compared to control subjects, as discussed in detail in the examples below.

In addition, in accordance with another embodiment of the present invention, the level of activity of a mitochondrial complex I enzyme is assayed in the presence or absence of a mitochondrial complex I inhibitor. Thus, the present invention provides a method for diagnosing schizophrenia in a subject by determining the inhibition of a mitochondrial complex I enzyme by a mitochondrial complex I enzyme inhibitor, and comparing the inhibition with a normative value of inhibition of the mitochondrial complex I enzyme wherein an altered inhibition of the mitochondrial complex I enzyme compared with the normative value is indicative of the subject having schizophrenia.

Inhibitors of mitochondrial complex I enzyme activity are catechols, such as for example dopamine, 6-hydroxydopamine, L-DOPA and norepinephrine (Ben-Schachar et al, 1995). Applicant and others have shown that catechols, primarily dopamine, can inhibit mitochondrial respiration by interfering with complex I both in vivo and in vitro (Ben-Schachar, 1995; Cohen, 1997; Przedborski et al., 1993, Ben-Shachar et al. 2004, Brenner-Lavie et al. 2008). In another embodiment, dopamine inhibits respiration through complex I by 30-40% but not through complex II, III. In another embodiment, dopamine inhibits respiration as described in Example 5. In another embodiment, antipsychotic drugs specifically inhibit complex I driven mitochondrial respiration. In another embodiment, Haloperidol, Clozapine, Chlorpromazine, specifically inhibit complex I driven mitochondrial respiration, while antidepressant such as Anafranil or Fluoxetine inhibit non-specifically as they inhibit through both complex I and complex II. In an other embodiment, Example 7 provides an embodiment of specific inhibition of complex I by antipsychotic drugs.

Cellular respiration is a functional measurement, which reflects impairment in mitochondrial enzymes and can be performed in blood cells freshly isolated or in immortal cell line such as in Epstein-Barr virus (EBV) transformed lymphocytes. The use of EBV transformed lymphocytes enables the measure of defect that is disease related and not medication related as it is accepted that after several passages, the effect of drugs is abolished.

In one embodiment, this invention provides a method for diagnosing schizophrenia in a subject, the method comprising the steps of: obtaining a sample from the subject; determining the cellular respiration through complex I enzyme; adding an inhibitor to the sample and determining the inhibition of the cellular basal respiration through complex I, wherein a decrease in respiration and/or an increase in inhibition of cell respiration through complex I enzyme as compared to cell respiration and its inhibitory values through complex I in a normative person is indicative to schizophrenic patients.

In an embodiment of the invention, this invention provides a method for diagnosing schizophrenia in a subject, the method comprising the steps of: obtaining a sample from the subject; determining the cellular basal respiration through complex I enzyme; adding an inhibitor to the sample and determining the inhibition of the cellular respiration through complex I, wherein a decrease in respiration by at least 30% and/or an increase in inhibition of cell respiration through complex I enzyme by using an inhibitor by more than 1.5 folds as compared to cell respiration and its inhibitory values through complex I in a normative person is indicative to a schizophrenic patient.

In another embodiment, the cellular respiration through complex I enzyme in schizophrenics is decreased by 20-40% as compared to normative person. In another embodiment, the cellular respiration through complex I enzyme in schizophrenics is decreased by 30-40% as compared to normative person. In another embodiment, the cellular respiration through complex I enzyme in schizophrenics is decreased by 30-80% as compared to normative person.

In another embodiment, the extent of inhibition of respiration is at least twice in schizophrenic patients than in normative person. In another embodiment, the extent of inhibition of respiration was at least 1.5 fold times more in a schizophrenic patient than in normative person. In another embodiment, the extent of inhibition of respiration is between 1.5-6 folds higher in a schizophrenic patient than in normative person. In another embodiment, the extent of inhibition of respiration is between 2-6 folds higher in a schizophrenic patient than in normative person.

In another embodiment of the invention, the cellular respiration inhibitor is an antipsychotic drug. In another embodiment of the invention, the inhibitor is a catechol such as L-DOPA, dopamine and norepinephrine (NE). In another embodiment of the invention, the inhibitor is Haloperidol, Clozapine, Chlorpromezine, or any combination thereof.

In one embodiment of the invention, the method of diagnosing schizophrenia in a subject by determining the inhibition of cell respiration comprises the step of obtaining a sample from a subject. In an embodiment, the sample is freshly isolated blood cells. In another embodiment of the invention, the sample is EBV transformed lymphocytes. In another embodiment of the invention, the sample is an immortal blood cell line.

Applicant has found that the inhibition of mitochondrial complex I enzyme by dopamine is altered in some schizophrenic patients compared with a normative value of inhibition in control subjects. For example. Applicant has demonstrated a significant increase in inhibition of complex I activity by dopamine in mitochondria from platelets of schizophrenic patients in acute exacerbation compared to control subjects, as discussed in detail in the examples below. In contrast, a similar level of inhibition of mitochondrial complex I activity in mitochondria from platelets of patients with recurrent major depression and patients with bipolar disorder compared to control subjects was observed, as discussed in detail in the examples below.

In accordance with yet another embodiment of the present invention, mitochondrial complex I is assayed by measuring the level of the complex subunits protein or mRNA encoding thereof. Thus, the present invention provides a method for diagnosing schizophrenia in a subject by determining the level of m-RNA or protein of a subunit of mitochondrial complex I in a sample obtained from the subject, and comparing the level of m-RNA or protein of the subunit mitochondrial complex I in the sample with a normative value of mitochondrial complex I m-RNA or protein. An altered level of at least one mitochondrial complex I subunit m-RNA or protein in the sample from the subject as compared to the normative value is indicative of the subject having schizophrenia.

In operation, the level of m-RNA or protein of mitochondrial complex I is determined by determining the level of m-RNA or protein of a subunit of mitochondrial complex I. Mitochondrial complex I is constituted from about 45 polypeptides, some of which are encoded by the nuclear DNA and others by mitochondrial DNA. For the purpose of this invention, any of the subunits may be studied. For example, in an embodiment of the invention, subunits that are encoded by the nuclear DNA may be studied.

Examples of subunits of mitochondrial complex I are: 1) 24- and 51 kDa subunits, which are iron-sulfur flavoprotein, which have catalytic properties including the site for transhydrogenation from NADH to NAD+; 2) the 75 kDa subunit, the largest iron-sulfur protein. Applicant has found that the level of m-RNA and protein of the 24 and 51 kDa subunits significantly increases in platelets or lymphocytes of schizophrenic patients compared with control subjects. In contrast, no change was found in the 75 kDa subunit, as discussed in detail in the examples below; 3) NDUFV1 subunit gene encodes the 51-kD subunit of complex I of the mitochondrial respiratory chain; 4) NDUFV2 subunit gene encodes the 24-kD subunit of complex I of the mitochondrial respiratory chain; and 5) NDUFS1 subunit gene encodes the 75-kD subunit of complex I of the mitochondrial respiratory chain.

In an embodiment of the invention, m-RNA levels can be determined according to standard techniques, using reverse transcriptase polymerase chain reaction (RT-PCR) technology. RT-PCR technology is generally described in *PCR Protocols: A Guide to Methods and Applications*, (Academic Press, San Diego, Calif., 1990). Reactions and manipulations involving other nucleic acid techniques are described in Sambrook et al., *Molecular Cloning: A Laboratory Manual*, (Cold Springs Harbor Laboratory Press).

In an embodiment of the invention, m-RNA levels can be determined according to standard techniques, for example without limitation by using real time quantitative PCR. technology. Real time quantitative PCR enables both detection and quantification (as absolute number of copies or relative amount when normalized to DNA input or additional normalizing genes) of a specific sequence in a DNA sample. Real-time polymerase chain reaction is combined with reverse transcription polymerase chain reaction to quantify low abundance messenger RNA (mRNA), enabling to quantify relative gene expression at a particular time, or in a particular cell or tissue type. In another embodiment, cDNA is synthesized by reverse transcription and is employed as a template in conducting the real time quantitative PCR.

Protein levels can be determined according to standard techniques, as described in Sambrook et al. Briefly, a sample obtained from a subject is contacted with a binding protein which specifically binds to a subunit of mitochondrial complex I, and the amount of complex formed between the binding protein and the subunit of mitochondrial complex I is determined.

In an embodiment of the invention, the binding protein is an antibody which specifically binds to a subunit of mitochondrial complex I. In another embodiment, the binding protein is an antibody which specifically binds to the 24 kDa subunit of mitochondrial complex I. In another embodiment, the binding protein is an antibody which specifically binds to the 51 kDa subunit of mitochondrial complex I. In another embodiment, the binding protein is an antibody which specifically binds to the 75 kDa subunit of mitochondrial complex I.

In an embodiment of the invention, the binding protein has a detectable label bound thereto, and the complex between the binding protein-label and the subunit of mitochondrial complex I is determined by visualizing the complex.

As defined herein, "contacting" means that the binding protein is introduced into the sample in a test tube, flask, tissue culture, chip, array, plate, microplate, capillary, or the like, and incubated at a temperature and time sufficient to permit the binding component to bind to a cell or a fraction thereof or plasma/serum or a fraction thereof containing the target. Methods for contacting the samples with the binding proteins, or other specific binding components are known to those skilled in the art and may be selected depending on the type of assay protocol to be run. Incubation methods are also standard and are known to those skilled in the art.

"Visualizing" the complex of label and binding protein of each of the subunits of mitochondrial complex I may be carried out by any means known in the art, including, but not limited to, ELISA, radioimmunoassay, flow cytometry, dot blots, western immunoblotting combined with gel electrophoresis, immunohistochemistry, HPLC and mass spectrometry.

"Specifically binds to", when referring to a protein or peptide, refers to a binding reaction which is determinative of the presence of a subunit of mitochondrial complex I in the presence of a heterogeneous population of proteins and other biologics other than the subunit. Thus, the immunoassay conditions, the specified antibodies bind to the specific mitochondrial complex I subunit antigens and do not bind in a significant amount to other antigens present in the sample. Specific binding to an antibody under such conditions may require an antibody that is selected for its specificity for a particular protein. For example, antibodies raised to the human mitochondrial complex I 24 kDa subunit immunogen described herein can be selected to obtain antibodies specifically immunoreactive with the mitochondrial complex I 24 kDa subunit proteins and not with other proteins. In another example, antibodies raised to the human mitochondrial complex I 51 kDa subunit immunogen described herein can be selected to obtain antibodies specifically immunoreactive with the mitochondrial complex I 51 kDa subunit proteins and not with other proteins. In another example, antibodies raised to the human mitochondrial complex I 75 kDa subunit immunogen described herein can be selected to obtain antibodies specifically immunoreactive with the mitochondrial complex I 75 kDa subunit proteins and not with other proteins. One can use immunoassays to detect for the complex formed between the binding protein and the subunit of mitochondrial complex I. A general overview of the applicable technology is in Harlow and Lane (1988). Furthermore, a description of general immunometric assays of various types can be found in U.S. Pat. Nos. 4,376,110 (David et al.) or 4,098,876 (Piasio).

Specifically, detection and quantification include but are not limited to precipitation of the protein containing the biomarker by an antibody which binds to the biomarker; competitive immunoassays; Western immunoblotting in which the biomarker (either as part of mixture or contained in an immunoprecipitated complex) is separated by gel electrophoresis, transferred to a suitable support (e.g. nitrocellulose) and visualized by reaction with an antibody(ies); radioimmunoassay, in which the degree to which the protein competes with a radioactively labeled standard for binding to the antibody is used as a means of detecting and quantifying the protein; and enzyme-linked immuno-sorbant assay (ELISA). ELISA is a known technique for quantifying proteins in which an antibody against the protein of interest is immobilized on an inert solid, e.g., polystyrene. A sample to be assayed for the protein of interest is applied to the surface containing immobilized antibody. Protein binds the antibody, forming a complex. This complex is then contacted by a second antibody which binds the same protein and which is covalently bound to an easily assayed enzyme. After washing away any of the second antibody which is unbound, the enzyme in the immobilized complex is assayed, providing a measurement of the amount of protein in the sample. The ELISA procedure can be reversed, i.e., the antigen is immobilized on an inert support (e.g. 96-well microplate) and samples are probed for the presence of antibody to the immobilized antigen. The biomarker can also be detected and its localization determined in cells and tissues using immunohistochemical procedures.

Further, cells may be detected using standard flow cytometry analysis using FACscan analyzer (Becton Dickinson, San Jose, Calif.). Cytometric techniques are known to those skilled in the art. For example the following describe such techniques and are hereby incorporated by reference in their entirety; U.S. Pat. No. 5,298,426 Method of differentiating erythroblasts from other cells by flow cytometry; U.S. Pat. No. 5,296,378 Method for classifying leukocytes by flow cytometry; U.S. Pat. No. 5,270,548 Phase-sensitive flow cytometer; U.S. Pat. No. 5,247,340 Flow imaging cytometer; U.S. Pat. No. 5,179,026 Method of classifying leukocytes by flow cytometry. Reagents used in the cytometric method include and are hereby incorporated by reference in their entirety: U.S. Pat. No. 5,175,109 Reagent for classifying leukocytes by flow cytometry; U.S. Pat. No. 5,167,926 Apparatus for pretreating cells for flow cytometry; U.S. Pat. No. 5,160,974 Closed sample cell for use in flow cytometry; U.S. Pat. No. 5,159,403 Flow cell mechanism in flow imaging cytometer; U.S. Pat. No. 5,159,398 Flow imaging cytometer; U.S. Pat. No. 5,150,313 Parallel pulse processing and data acquisition for high speed, low error flow cytometry U.S. Pat. No. 5,144,224 Millimeter wave flow cyrometer; U.S. Pat. No. 5,093,234 Method of aligning, compensating, and calibrating a flow cytometer for analysis of samples, and microbead standards kit therefor; U.S. Pat. No. 5,073,497 Microbead reference standard and method of adjusting a flow cytometer to obtain reproducible results using the microbeads U.S. Pat. No. 5,039,613 Reagents used in a method of classifying leukocytes cytometry U.S. Pat. No. 5,032,381 Chemiluminescence-based static and flow cytometry; and U.S. Pat. No. 4,954,715 Method and apparatus for an optimized multiparameter.

In an embodiment of the invention, western blotting is a method of detection of the protein level of mitochondrial complex I subunit that is suitable for the present invention.

Either monoclonal or polyclonal antibodies (as well as any recombinant antibodies) specific for the subunit of mitochondrial complex I can be used in the various immunoassays. Polyclonal antibodies against peptides of a specific subunit of mitochondrial complex I may be produced by immunizing animals using the selected peptides. Alternatively, monoclonal antibodies may be produced by in vitro techniques known to a person of ordinary skill in the art. For example, monoclonal antibodies are prepared using hybridoma technology by fusing antibody producing B cells from immunized animals with myeloma cells and selecting the resulting hybridoma cell line producing the desired antibody. The antibodies directed to the subunits of mitochondrial complex I may be coupled to a solid-phase support, e.g., nitrocellulose, nylon, column packing materials (e.g., Sepharose beads), magnetic beads, on a chip, array, glass wool, plastic, metal, polymer gels, cells, or other substrates. Such supports may take the form, for example, of beads, wells, dipsticks, or membranes. The antibodies may be detectably labeled, utilizing conventional labeling techniques well-known to the art. As used herein, the term "label" refers to a molecule, which may be conjugated or otherwise attached (i.e. covalently or non-covalently) to a binding protein as defined herein. Labels are known to those skilled in the art. Thus, the antibodies may be labeled with radioactive isotopes, non-radioactive isotopic labels, fluorescent labels, enzyme labels, chemiluminescent labels, bioluminescent labels, free radical labels, or bacteriophage labels, using techniques known in the art. Examples of radioisotopic labels are H, $^{125}$I, $^{131}$I, $^{35}$S, $^{14}$C. etc. Examples of non-radioactive isotopic labels are $^{55}$Mn, $^{56}$Fe, etc.

Examples of fluorescence labels are fluorescent labels which are directly labeled with a fluorescence label, or fluorescent labels which are indirectly labeled with a fluorescence label. In the last case, the fluorescence label is conjugated to a secondary antibody, which is directed against the first antibody, such as an anti species Ig antibody. Typical fluorescent labels include, but are not limited to a fluorescein label, an isothiocyanate label, a rhodamine label, a phycoerythrin label, etc., for example fluorescein isothiocyanate (FITC, International Biological Supplies, Melbourne, Fla.), rhodamine, phycoerythrin (P.E., Coulter Corp., Hialeah, Fla.), phycocyanin, alophycocyanin, phycoerythrin-cyanin dye 5 (PECy5, Coulter), label, a phycocyanin label, an allophycocyanin label, an O-phthaldehyde label, a fluorescamine and Texas Red.

Examples of enzyme labels include alkaline phosphatase, beta-galactosidase, glucose-6-phosphate dehydrogenase, maleate dehydrogenase, and peroxidase. Two principal types of enzyme immunoassay are the enzyme-linked immunosorbent assay (ELISA), and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; the activity can thus be measured without the need for a separation step.

Particularly suitable labels include those, which permit analysis by flow cytometry, e.g., fluorochromes. Other suitable detectable labels include those useful in colorimetric enzyme systems, e.g., horseradish peroxidase (HRP) and alkaline phosphatase (AP). Other proximal enzyme systems are known to those of skill in the art, including hexokinase in conjunction with glucose-6-phosphate dehydrogenase.

Additionally, chemiluminescent compounds may be used as labels. Chemiluminescent labels, such as green fluorescent proteins, blue fluorescent proteins, and variants thereof are known. Also bioluminescence or chemiluminescence can be detected using, respectively, NAD oxidoreductase with luciferase and substrates NADH and FNIN or peroxidase with luminol and substrate peroxide. Typical chemiluminescent compounds include luminol, isoluminol, aromatic acridinium esters, imidazoles, acridinium salts, and oxalate esters. Similarly, bioluminescent compounds may be utilized for labelling, the bioluminescent compounds including luciferin, luciferase, and aequorin. Once labeled, the antibody may be employed to identify and quantify immunologic counterparts (antibody or antigenic polypeptide) utilizing techniques well-known to the art.

In a further embodiment of this invention, commercial test kits are disclosed which are suitable for use to determine the level of activity and/or level or m-RNA and/or level of protein of mitchondrial complex I, in order to diagnose whether a subject has schizophrenia.

In accordance with the testing techniques discussed above, one class of such kits will contain a container for containing a sample from the subject, at least one reagent for determining the level of activity of a mitochondrial complex I enzyme; and at least one buffer or solution. The container may be any container which can contain the sample, such as a vial, lube, flask, box, bottle and the like.

The activity of mitochondrial complex I enzyme is determined using any of the methods described hereinabove. For example, when the activity of mitochondrial complex I is determined by monitoring the activity of NADH dehdrogenase, the kit comprises reagents for determining the activity of NADH dehydrogenase, such as NADH and an electron acceptor. In an embodiment of the invention, the electron acceptor is a biological electron acceptor, such as ubiquinone. In another embodiment, the electron acceptor is an artificial electron acceptor, such as ferricyanide, for example potassium ferricyanide. Other reagents, buffers and solutions for an NADH dehydrogenase assay are disclosed in Singer et al. (1974); Estornell (1993); Hatefi (1978); and Ragam (1987) and described in detail in the examples below. The kit may also contain peripheral reagents such as buffers, stabilizers, etc.

In accordance with the testing techniques discussed above, another class of such kits will contain a container for containing a sample from the subject, at least one reagent for determining the level of m-RNA or protein of mitochondrial complex I, and at least one buffer or solution.

Reagents for determining the level of m-RNA of mitochondrial complex I include specific primers for a subunit of mitochondrial complex I. For example, in an embodiment of the invention, the kit includes 5' and 3' primers for the 24 kDa subunit of mitochondrial complex I. In another embodiment, the kit includes 5' and 3' primers for the 51 kDa subunit of mitochondrial complex I. In another embodiment, the kit includes 5' and 3' primers for the 75 kDa subunit of mitochondrial complex L. Other reagents used are standard reagents, buffers and solutions for RT-PCR reactions, such as described in PCR Protocols: A Guide to Methods and Application (Academic Press, San Diego, Calif., 1990). Suitable reagents for determining the level of protein of mitochondrial complex I include antibodies that specifically bind to a subunit of mitochondrial complex I. For example, in an embodiment of the invention, the kit comprises an antibody that binds to the 24 kDa subunit of mitochondrial complex I. In another embodiment, the kit comprises an antibody that binds to the 51 kDa subunit of mitochondrial complex I. In another embodiment, the kit comprises an antibody that binds to the 75 kDa subunit of mitochondrial complex I. The antibodies may be labeled to enable detection, as described above. Detection of antibodies is done by standard techniques, as described in Sambrook et al., *Molecular cloning: A laboratory Manual* Cold Springs Harbor Laboratory Press).

The above discussion provides a factual basis for the use of mitochondrial complex I as a biological marker in the diagnosis of schizophrenia. The methods used with and the utility of the present invention can be shown by the following non-limiting examples and accompanying figures. This section is set forth to aid in an understanding of the invention but is not intended and should not be construed to limit in any way the invention as set forth in the claims that follow thereafter.

EXAMPLES

Example 1

Determination of Mitochondrial Complex I Activity in Schizophrenic Patients, Patients with Affective Disorders and Normal Subjects Complex I activity was determined by measuring NADH ferricyanide reductase activity or NADH ubiquinone reductase activity in medicated and unmedicated schizophrenic patients, patients with recurrent major depression, patients with bipolar disorder, the depressed type and healthy controls (Ben-Schachar et al, 1999).

Materials and Methods

Subjects

A total of 77 patients and 24 control subjects participated in the study. All patients met DSM-IV criteria for schizophrenia (acute exacerbation), bipolar disorder (BD) depressed type or recurrent major depression (MDD). Consensus diagnosis by two senior psychiatrists was based on extended clinical interviews and reviews of patients' charts. Patients with schizoaffective illness were excluded. Twenty-four subjects without prior psychiatric history served as a control group. This group was age and sex matched to the schizophrenic group. Table 1 displays some of the demographic characteristics of the study groups. All schizophrenic patients (n=50) were in a state of acute psychotic exacerbation. At the time of blood sampling, 25 had been medication-free for at least one month and most patients had not received medication for significantly longer periods. Prior to hospitalization these unmedicated patients were all in a residual state, had dropped out of psychiatric follow-up and had discontinued medication due to lack of compliance. Once psychotic symptoms re-occurred, these patients returned for treatment. Upon admission, a short-acting benzodiazepine was used when necessary to control agitation and restlessness until blood was collected, after which antipsychotic treatment was started. The remaining 25 schizophrenic patients were receiving at the time of the study various antipsychotic medications at conventional doses, including haloperidol (n=7), chlorpromazine (n=6), perphenazine (n=4), clozapine (n=6) and resperidone (n=2). Some received additional anticholinergic medications and benzodiazepines. Most of the patients were exposed to prolonged antipsychotic medication. MDD patients (n=17) received an antidepressant treatment, mostly selective serotonin reuptake inhibitors, or tricyclic antidepressants. BD patients (n=10), all depressed at the time of the study, were on a combination of a mood stabilizers and antidepressants. Patients who needed additional medications for other medical conditions were excluded. All patients were given an explanation of the purpose of the study and provided a written informed consent.

Mitochondrial Enzyme Activity

Mitochondrial respiratory chain enzymes activity was assayed blindly and in triplicate after two cycles of freezing and thawing in a final volume of 1 ml at 25° C. by standard techniques. Alternatively, 1% digitonin was added for 1 min and subsequently diluted 1:100 by the addition of the buffer before the start of the reaction. Briefly, complex I activity was assayed by two different methods using either ubiquinone (CoQ) or ferricyanide as electron acceptors.

NADH Ferricyanide Reductase Activity

NADH ferricyanide reductase activity was determined at $V_{max}$ ferricyanide throughout the study with or without antimycin A (Singer, 1974). Kinetic analysis was performed in mitochondrial preparation (0.25 mg protein/ml) at 25° C. in 50 mM Tris-HCl buffer pH 7.4 containing 0.25 M sucrose. Mitochondria were disrupted by pretreatment either by thawing and freezing, or with 1% digitonin for 1 min, subsequently diluted 1:100 by the addition of the buffer before the start of the reaction. There was no difference between both procedures. The reaction was started by the addition of 0.1 mM potassium ferricyanide and 0.14 mM NADH with and without 10 μg antimycin A. The decrease in NADH absorbance was followed at 340 nm for 1 min with a 3 sec interval between successive readings and 1 sec initial delay. In this

TABLE 1

Clinical data for the various groups

|  | Controls | Schizophrenic patients | | Depressed patients | |
|---|---|---|---|---|---|
|  |  | Medicated | Unmedicated | MDD | BP |
| No. of patients | 24 | 25 | 25 | 17 | 10 |
| Gender (F/M) | 13/11 | 10/15 | 14/11 | 11/6 | 6/4 |
| Age ± SD (range) | 35.0 ± 9.8 (22-50) | 25.9 ± 7.0 (18-43) | 32.0 ± 13.0 (18-60) | 53.0 ± 14.0[a] (33-75) | 50.0 ± 13.5[b] (27-75) |
| Duration of Illness (range) |  | 5.2 ± 5.5 (0.5-20) | 4.2 ± 10.0 (0.5-20) | 10.3 ± 10.3 (0.5-34) | 18.0 ± 11.1[c] (2-41) |

A significant difference for age and duration of illness was demonstrated in depressed patients as compared with the schizophrenic or control groups, which did not differ from each other. The significance of the difference (df = 100 F = 19.291 p < 0.0001 for age of subjects; df = 76 F = 6.720 p = 0.0005 for duration of illness) was analyzed by one way ANOVA followed by Bonferroni.
[a]p < 0.001 (t = 5.033);
[b]p < 0.01 (t = 3.533) vs. control,
[c]p < 0.01 (t = 5.367) vs. schizophrenic patients.

Isolation of Mitochondria from Platelets

Blood (40-80 ml) was collected from the cubital vein without tourniquet between 8:00 and 10:00 a.m., mixed 9:1 with 3.8% (w/v) tri-sodium citrate, and platelet-rich plasma (PRP) separated at room temperature by centrifugation at 200×g for 20 min. Platelets were isolated and washed with Tyrode's buffer pH 7.4 containing 1 mM EDTA as described previously (Krige et al., 1992). The platelet pellet was gently resuspended in ice cold 10 mM Tris buffer pH 7.4 containing 250 mM sucrose and 1 mM EDTA and disrupted by a Dounce A homogenizer (20-30 strokes). The breakdown of the platelets was verified by light microscopy. The homogenate was centrifuged at 1000×g at 4° C. for 20 min to remove unbroken cells. The supernatant, containing the cytoplasmic extract was centrifuged at 12,000×g at 4° C. For 15 min and an enriched mitochondrial fraction was isolated on percoll as described previously (Ben-Shachar et al., 1995; Gavin et al., 1990; McComark and Denton, 1989). Electron microscopy showed a sediment of intact mitochondria with dense granules and α-granules. The final preparation was immediately stored at −70° C. until use.

mitochondrial preparation rotenone had no effect on NADH ferricyanide reductase activity.

NADH-CoQ Reductase Activity

NADH-CoQ reductase activity was assayed in 20 mM potassium-phosphate buffer pH 7.2 containing 5 mM $MgCl_2$ and 1 mM KCN. NADH 0.14 mM and 50 μM decylubiquinone (2,3-dimethoxy-5-methyl-6-decyl-1,4-benzoquinone) were added with and without 10 μM rotenone or 10 μg antimycin A as described previously (Estorneli, 1993; Hatefi, 1978; Ragan et al., 1987). The residual activity of NADH CoQ reductase in the presence of rotenone was 5-15%.

Results from both assays for each sample are expressed as the difference between reductases activities in the absence and the presence of the relevant inhibitors.

For Dopamine inhibition studies, aliquots of samples were incubated with or without dopamine 10 exp (−5) M for one minute prior to initiation of the reaction. The level of activity of mitochondrial complex I was determined in the presence and absence of dopamine, using the methods described above.

Statistical Analysis

The results were analyzed according to standard statistical tests. Non-parametric descriptive statistics were used to avoid assuming a definite theoretical normal distribution of the data set. Parametric tests were performed to detect any difference between the various groups. Inter-group differences on the various dependent variables were assessed by one way ANOVA followed by Bonferroni post hoc multiple comparisons test. Linear regression analysis was used to estimate the relationship between NADH ferricyanide reductase and NADH CoQ reductase activities.

All chemicals for enzyme analyses were purchased from Sigma Chemical Co. St. Louis, Mo., USA. Protein concentration was measured using Biuret reaction.

Results

Correlation Between NADH Ferricyanide Reductase and NADH Coq Reductase Activities Complex I activity can be measured by two methods, using either CoQ or the artificial electron acceptor ferricyanide. The assay using ferricyanide is the most reliable and sensitive measure of NADH dehydrogenase activity (Singer, 1974); it has the added advantage that it requires only half the amount of blood. A highly significant correlation ($p<0.001$, $r=0.85$) was found between NADH ferricyanide reductase and NADH CoQ reductase activities in platelet mitochondria of 40 subjects from the various patients groups and healthy controls (not shown). Therefore, the rest of the study was carried out by measuring NADH ferricyanide reductase activity at $V_{max}$ ferricyanide.

NADH Ferricyanide Reductase Activity

Reference is now made to FIG. 1, which shows individual values of NADH ferricyanide reductase activity, which were markedly increased in mitochondrial preparation from platelets of schizophrenic patients in acute exacerbation compared with those from control subjects. In contrast, no difference in enzyme activity was observed between depressed patients with recurrent major depression, those with bipolar disorder and control subjects. Only a minimal overlap was observed between the individual values of schizophrenic patients and the remaining groups. Quantitatively, one way ANOVA revealed a significant difference between the groups (F=42.522; df=100 $p<0.0001$). A set of Bonferroni post hoc analyses showed that both the medicated and unmedicated schizophrenic groups were significantly different from controls (t=5.516 and t=4.790 for medicated and unmedicated schizophrenics, respectively $p<0.001$). The schizophrenic subjects were also significantly different from both groups with affective disorders (t>6.604, $p<0.001$ for all interactions between the schizophrenic groups and the affective disorders groups). Table 2 summarizes the means±SD of all groups.

Age was significantly different between patients with affective disorders and the remaining groups. ANCOVA control for age did not change the significance of the difference between the schizophrenic patients and the patients with affective disorders and control subjects.

NADH ferricyanide reductase activity was analyzed in schizophrenic patients who did not receive medication for various periods (for at least one month, and most patients had not received medication for significantly longer periods, up to several years). No significant difference was observed between patients who were unmedicated for 1-3 months and those who had not received medication for more than a year prior to the study. Sixty percent of the unmedicated patients received upon admission a single administration of a short acting benzodiazepine to control agitation and restlessness until blood was collected. No significant difference (t=0.08, p=0.9412) was observed between the two groups. Thus, all unmediated patients were pooled into one group. NADH ferricyanide reductase activity was similar in medicated and unmedicated schizophrenic patients.

The ability of Dopamine to inhibit NADH-ferricyanide reductase activity was investigated by pre-incubating samples from schizophrenic patients and from controls with dopamine prior to initiation of the enzyme assay. Dopamine inhibited NADH-ferricyanide reductase activity to a greater extent in schizophrenic patients compared with control subjects, subjects with major depression and subjects with bipolar disorder, as shown in Table 2.

TABLE 2

Mitochondrial NADH-ferricyanide reductase activity in platelets of schizophrenic patients, patients with affective disorders and control subjects.

| Subjects | NADH dehydrogenase activity (nmol/mg protein/min) | Dopamine inhibition (%) |
|---|---|---|
| Controls (n = 24) | 131.87 ± 53.1 | 38.6 ± 13.4 |
| Medicated schizophrenics (n = 25) | 319.60 ± 85.0* | 69.1 ± 19.9* |
| Unmedicated schizophrenics (n = 25) | 296.85 ± 54.7* | 72.6 ± 15.0* |
| Recurrent major depression (n = 17) | 136.21 ± 44.9 | 31.7 ± 16.5 |
| Bipolar disorder (n = 10) | 136.50 ± 57.7 | 34.5 ± 13.6 |

Values are means ± SD.

*$p<0.001$ vs. controls and vs. both groups of depressed patients was analyzed by Bonferroni post hoc test.

A crucial factor in any diagnostic assay is the reproducibility of the results. The reproducibility of complex I activity measure is demonstrated in Table 3.

TABLE 3

Sample reproducibility of complex I activity in control subjects

| Number of subject | Number of sampling | Complex I activity (nmol/mgProtein/min) |
|---|---|---|
| 1 | 4 | 199.28 ± 16.10 |
| 2 | 4 | 112.50 ± 16.10 |
| 3 | 2 | 167.14 ± 4.82 |
| 4 | 5 | 163.93 ± 15.43 |
| 5 | 3 | 72.32 ± 7.39 |
| 6 | 5 | 208.93 ± 19.28 |
| 7 | 2 | 159.11 ± 28.93 |
| 8 | 2 | 186.43 ± 4.02 |
| 9 | 3 | 393.75 ± 48.21 |

Intra-sample variation was determined by repeated measurements of complex I activity at various time points over a period of one year. Results are means ± SD.

NADH Ferricyanide Reductase Activity Normalized for Cytochrome c Oxidase Activity Cytochrome c oxidase was used as a marker for the estimation of mitochondrial mass and purity between samples.

To show that cytochrome c oxidase has similar activity in all groups, cytochrome c oxidase was assayed by following the decrease in the absorbance of reduced cytochrome c at 550 nm (Storrie and Madden, 1990).

Table 4 presents cytochrome c oxidase activity in platelet mitochondria from the various groups. No statistically significant differences were found among the groups.

TABLE 4

Cytochrome c oxidase activity in mitochondria from platelets of schizophrenic patients, patients with affective disorders and control subjects.

| Subjects | Cytochrome c oxidase activity (nmol/mg protein/min) |
|---|---|
| Controls (n = 24) | 39.20 ± 15.87 |
| Medicated schizophrenics (n = 25) | 33.29 ± 17.70 |
| Unmedicated schizophrenics (n = 25) | 45.69 ± 24.83 |
| Major depression (n = 17) | 34.81 ± 15.23 |
| Bipolar disorder (n = 10) | 30.9 ± 12.91 |

Values are means ± SD. The number of patients is given in parentheses. No statistically significant difference was obtained.

Figure 2:
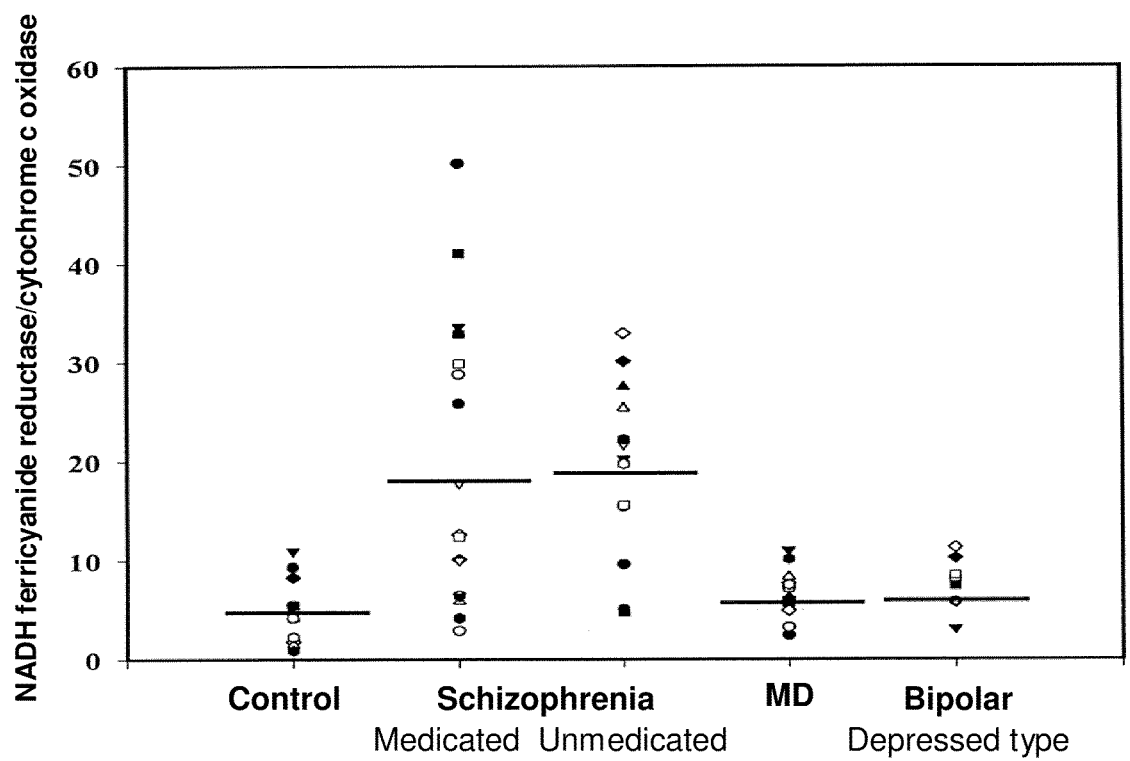
FIG. 2: depicts individual values of NADH ferricyanide reductase activity normalized for cytochrome c oxidase activity in medicated (MS) and unmedicated (US) schizophrenic patients, patients with major depression (MD) patients with bipolar disorder (BP), and control subjects (C).

Since cytochrome c oxidase showed similar activity in all groups, it was used as a marker for the estimation of mitochondrial mass and purity between samples. Reference is now made to FIG. 2, which shows NADH ferricyanide reductase activity normalized for cytochrome c oxidase activity. As shown in FIG. 2, normalization did not affect the previously described between-groups differences. Quantitatively, one way ANOVA revealed a significant difference among the groups (F=11.429; df=67 $p<0.0001$). A set of Bonferroni post hoc analyses showed that both schizophrenic groups were significantly different from the control group (t=4.951 and t=4.777 for medicated and unmedicated schizophrenic patients, respectively $p<0.001$). Both schizophrenic groups were significantly different from both groups of patients with affective disorders (t>3.714, $p<0.01$ in all cases). No significant difference was found in normalized complex I activity between medicated and unmedicated schizophrenic patients or between the two affective disorder group and control subjects.

Complex I Activity as a Function of Clinical State

Schizophrenic patients at various stages of the disease (patients at acute phase, residual patients with pronounced positive symptoms, and residual patients without pronounced positive symptoms who experience mainly negative symptoms) were recruited. Healthy control subjects were matched as much as possible for age and sex. All patients were formally diagnosed according to DSM-IV criteria and were evaluated by a senior psychiatrist using positive and negative symptom scale (PANSS). Complex I activity was significantly increased in both the acute patients and residual patients having pronounced positive symptoms as evaluated by PANNS, while patients in a residual state lacking pronounced positive symptoms showed a decrease in mitochondrial complex I activity (Table 5). A high correlation was found between most parameters of the positive category and complex I activity in the schizophrenic population (Table 6) with r=0.74; $p<0.001$ between total positive scores and activity. These results indicate that alteration in complex I activity is state dependent.

TABLE 5

Mitochondrial NADH frricyanide reductase (complex I) activity in platelets of schizophrenic patients at various disease stages.

| Subjects | Complex I activity (nmol/mg protein/min) |
|---|---|
| Controls (n = 48) | 218.23 ± 102.26 |
| Schizophrenics at acute phase (n = 56) | 419.96 ± 82.14*† |
| Chronic schizophrenics with positive symptoms (n = 22) | 402.23 ± 99.43*† |
| Chronic patients with residual schizophrenia (n = 23) | 115.84 ± 104.42** |

Values are means ± SD. The number of patients is given in parentheses.
*$p < 0.0001$,
**$p < 0.002$ vs. controls,
†$p < 0.0001$ vs. residual schizophrenia analyzed by Bonferroni post-hoc test.

TABLE 6

Pearson's correlation between complex I activity and clinical characteristics of 47 chronic schizophrenic patients

| Scale for assessment of positive symptoms | Pearson's correlation (r) | Significance (2-tailed) (p<) |
|---|---|---|
| delusion | 0.546 | 0.013 |
| hallucination | 0.53 | 0.016 |
| excitement | 0.513 | 0.021 |
| grandiosity | 0.715 | 0.0001 |
| suspiciousness | 0.608 | 0.004 |
| hostility | 0.741 | 0.0001 |
| All positive | 0.704 | 0.001 |
| General | 0.667 | 0.001 |
| Sum of symptoms | 0.455 | 0.044 |

Twenty schizophrenic patients were evaluated by using Positive and Negative Symptom Scale (PANSS) for schizophrenia. Ten showed pronounced positive symptoms and ten patients were in a residual state. Results show only the symptoms which showed significant correlation with complex I activity.

Example 2

Complex I Alteration is Expressed at the Level of Translation of its 24 and 51 kDA Subunit but not the 75 kDA Subunit Materials and Methods RNA Extraction RNA extraction from blood cells (lymphocytes, platelets leukocytes etc) is performed using RNA isolation kit. Homogenization is carried out by the addition of 1 ml RNA STAT-60 (or as described by any other extraction kit) per 50-100 mg tissue and extraction is performed according to the kit instructions. For further purification of the RNA 1 volume of phenol: chloroform: isoamyl alcohol (25:24:1) is added to 1 volume of the aqueous layer. Following vortex the layers are separated by centrifugation at 9.000 g for 5 min. The upper layer is separated and RNA is precipitated by adding 0.5 volume of isopropanol, centrifugation at 10,500 g for 15 minutes. Subsequently washing is done by 75% ethanol and centrifugation as above. All RNA preparations are then dissolved in RNase free water and treated by DNase. DNAase treated RNA is purified by an equal volume of phenol: chloroform: isoamyl alcohol (25:24:1). The aqueous layer is separated by centrifugation as detailed above, and an equal volume of chloroform was added. RNA is then precipitated from the aqueous phase by ¹/₁₀ volume of NaOAc (pH 4.5) and 2.5 volumes of 95% ethanol by centrifugation at 10.500 g for 15 minutes. The pellet was washed again with 80% ethanol centrifuged as before, dried, dissolved in RNase free water and stored in −80° C. until use. RNA integrity depicted in the form of three bands corresponding to 28S, 18S and 5S RNA is assessed by electrophoresis in a 1% agarose/formaldehyde gel stained with ethidium bromide. The amount of RNA extracted is determined spectophotometricaly at 260 nm.

Reverse Transcription (RT)

After extraction of total RNA, reverse transcription was performed forming a single strand cDNA. Following incubation at 72° C., 5 µg of total RNA was reverse transcribed for 1 h at 37° C. with 0.5 µg random primers in the presence of 200 units of M-MLV reverse transcriptase (Promega), 25 units of RNasin ribonuclease inhibitor and 500 µM final concentration of dNTP in a 25 µl reaction.

Quantitative PCR (Q-PCR)

Q-RT-PCR assessment is performed on reversed transcribed RNA using LightCycler with FastStart DNA Master SYBR Green I ready-to use PCR mix kits (Roche Diagnostics, Mannheim, Germany). Each experimental set includes one reaction with water as a template to control for cross contamination, a standard curve and 3 reference genes. Amplified products is visualized on 1.5% agarose gel. The results are analyzed in real-time using the provided program of the LightCycler or any other apparatus for qPCR, and normalized against reference genes in order to correct sample-to-sample variation. Genes like Glyceraldehydes-3-phosphate dehydrogenase (GAPDH), β-Actin and 18S rRNA serve as reference genes for normalization. For each of the complex I, 45 genes (including NDUFV1, NDUFV2 and NDUFS1 or 51-kDa, 24-kDa and 75 kDa, respectively) cDNA (100-0.4 ng/5 µl) are added to 10 µl SYBER Mix (AB absolute Syber Green ROX mix) or any other commercially available mix for Q-PCR, such as those containing TaqMan, 2 µl of primer mix (forward+reverse, 500 nM of each) and 3 µl of $H_2O$ to give a final volume of 20 µl. Each experimental set contains 96 samples. Each sample is analyzed in duplicates.

RT-PCR Analysis

The expression of 24-, 51- and 75-kDa subunits of complex I in platelets was studied by using the RT-PCR technique. Total RNA was isolated using RNA STAT-60 kit (TEL-TEST, INC.). For cDNA synthesis and PCR amplification Reverse Transcriptase kit from Promeca and FastStart kit from Roche Molecular Biochemicals were used. A single cDNA strand was synthesized by reverse transcriptase reaction. 5 µg of total RNA were incubated with 1 µg Random Primer at 70° C. for 5 min before the addition of 8 µl 5×MMLV, 20 mM dNTP mix, 24 units of RNasine and 400 units of MMLV Reverse Transcriptase. Double-distilled DEPC water was added to a final volume of 40 µl. The assay mixture was incubated at 37° C. for 1 hour and then at 95° C. for 5 min. Amplification of ssDNA of the subunits was performed by PCR reaction. PCR incubation mixture contained 25 mM dNTP mix, 2.5 µl of 10×PCR buffer plus 20 mM $MgC_2$, 5 mM $MgCl_2$, 5×GC-RICH solution, 1 unit of FastStart Taq DNA Polymerase, 10 pM 3' primer, 10 pM 5' primer and 1.5 µl of RT-product. Double-distilled water was added to a final volume of 25 µl. The mixture was incubated in a T3 Thermocycler with first denaturation at 95° C. for 5 minutes; the following denaturation at 95° C. for 1 minute, annealing at 60° C. for 1 minute, extension at 72° C. for 1 minute; for 38 cycles of amplification with final extension at 72° C. for 10 minutes. The region amplified by PCR was between 120 and 760 bases forming a 641 bp fragment for 24 kDa; between 211 and 637 bases forming a 427 bp fragment for 51 kDa; between 1231 and 2230 bases forming a 1000 bp fragment for 75 kDa. RT-PCR products were assessed in a 2% agarose gel containing ethidium bromide A 2645-36 bp DNA ladder (NOVEX) was used as a base pair reference marker. To control for the quality of RT-PCR assay and to prevent cross contamination, RNA extraction, RT-PCR assay set-up and post-RT-PCR product analysis were carried out separately. A parallel PCR reaction was performed with a pair of sense and antisense β-actin specific primers, for normalizing variations in RNA aliquots taken for RT reaction and gel loading.

Subjects

The total number of subjects assayed for mRNA levels:

| Subunit | Controls | Schizophrenic patients |
|---------|----------|------------------------|
| 24 kDa  | 17       | 43                     |
| 51 kDa  | 19       | 31                     |
| 75 kDa  | 12       | 32                     |

Results

Reference is now made to FIG. 3, which depicts RT-PCR analysis from platelets of schizophrenic patients at acute relapse and healthy control subjects. mRNA levels of 24 kDa subunit (FIG. 3A) and 51 kDa subunit (FIG. 3B) of complex I, measured by RT-PCR, were higher by more than 3 and 2 folds, respectively, in schizophrenic patients as compared to controls. In contrast, no change was found in the 75 kDa subunit (FIG. 3C). FIG. 3D depicts mRNA levels of β-actin, for normalizing variations in RNA aliquots taken for RT reaction and gel loading. Table 7 summarizes m-RNA levels of the 51 kDA subunit of mitochondrial complex I from several gels, normalized for beta-actin. Table 8 summarizes m-RNA levels of the 24 kDA subunit of mitochondrial complex I from several gels, normalized for beta-actin. Table 9 summarizes protein levels of the 24 kDA and 51 kDA subunits of mitochondrial complex I from several gels, normalized for beta-actin. The brackets indicate the number of samples for each gel. As can be seen, the mRNA ratio between schizophrenic patients and control while measuring the 51 kDA subunit is between about 1.8-3.18 and the mRNA ratio between schizophrenic patients and control while measuring the 24 kDA subunit is between about 1.6-6.0.

TABLE 7

Summary of densitometry evaluation of m-RNA levels of the 51 kDA subunit of mitochondrial complex I from several gels

| No. of Gel C/P | Control subjects (OD) | Schizophrenic patients (OD) | Patients/Controls (OD) |
|----------------|-----------------------|-----------------------------|------------------------|
| 1 (7/11)       | 1.030 ± 0.147         | 1.830 ± 0.189               | 1.8                    |
| 2 (4/4)        | 1.411 ± 0.029         | 3.821 ± 0.329               | 2.7                    |
| 3 (3/4)        | 4.498 ± 0.461         | 7.180 ± 0.844               | 2.3                    |
| 4 (4/4)        | 0.731 ± 0.196         | 1.700 ± 0.269               | 2.3                    |
| 5 (1/1)        | 0.129                 | 0.343                       | 2.7                    |
| 6 (1/1)        | 0.82                  | 1.62                        | 1.98                   |
| 7 (1/1)        | 0.466                 | 1.48                        | 3.18                   |

TABLE 8

Summary of densitometry evaluation of m-RNA levels of the 24 kDA subunit of mitochondrial complex I from several gels

| No. of Gel Control/patient | Control subjects (OD) | Schizophrenic patients (OD) | Patients/Controls (OD) |
|----------------------------|-----------------------|-----------------------------|------------------------|
| 1 (7/11)                   | 0.971 ± 0.135         | 3.207 ± 0.452               | 3.3                    |
| 2 (8/8)                    | 0.017 ± 0.003         | 0.092 ± 0.021               | 5.3                    |
| 3 (4/4)                    | 2.997 ± 0.360         | 7.758 ± 1.292               | 2.58                   |

TABLE 8-continued

Summary of densitometry evaluation of m-RNA levels of the 24 kDA subunit of mitochondrial complex I from several gels

| No. of Gel Control/patient | Control subjects (OD) | Schizophrenic patients (OD) | Patients/Controls (OD) |
|---|---|---|---|
| 4 (3/4) | 4.498 ± 0.461 | 7.180 ± 0.844 | 1.60 |
| 5 (1/1) | 0.11 | 0.66 | 6.00 |
| 6 (1/1) | 0.82 | 1.62 | 1.98 |
| 7 (1/1) | 0.466 | 1.48 | 3.18 |

TABLE 9

Summary of densitometry evaluation of protein levels of the 24 kDA and the 51 kDA subunits of mitochondrial complex I from several gels

| No. of Gel (C/P) | Control subjects (OD) | Schizophrenic patients (OD) | Patients/Controls (OD) |
|---|---|---|---|
| 24 kDa subunit | | | |
| 1 (5/6) | 1.191 ± 0.153 | 6.218 ± 0.146 | 5.1 |
| 2 (4/4) | 1.261 ± 0.062 | 1.798 ± 0.120 | 1.4 |
| 3 (5/6) | 0.712 ± 0.086 | 1.274 ± 0.140 | 1.8 |
| 51 kDa subunit | | | |
| 1 (5/6) | 0.716 ± 0.076 | 1.021 ± 0.0471 | 1.4 |
| 2 (4/4) | 0.786 ± 0.045 | 1.247 ± 0.123 | 1.6 |
| 3 (5/6) | 0.413 ± 0.047 | 1.491 ± 0.233 | 3.6 |

Example 3

Complex I Alteration is Expressed at the Level of Protein of Its 24 and 51 kDA Subunits Materials and Methods
Western Blot Analysis Platelets were isolated from 20 ml blood, washed with Tyrode's buffer pH 7.4 containing 1 mM EDTA according to Krige et al. (1992) and centrifuged at 1000 g for 15 min at 4. Pellet was suspended in 10 mM Tris buffer pH 7.4 containing 250 mM sucrose, 0.5% NP40 and TM protease inhibitor cocktail. Samples were placed on ice for 1 hour with in between vortex (4-5 times). The suspension was centrifuged at 10,000 rpm for 5 min. The supernatant (100-120 h+g total protein) was diluted 1:1 in electrophoresis sample buffer containing 20% (v/v) glycerol, 4% (w/v) SDS, 250 mM Tris-HCl, pH 6.8, 10% (v/v) 2-mercaptoethanol, 0.5 mg/ml bromophenol blue. To control for the amount of protein loaded, protein concentration was measured using Bradford reagent (BIO-RAD). The protein sample was separated on a SDS acrylamide gel (14% and 7.5% gel for 24 kDa and 51 kDa subunits, respectively) and transferred to a nitrocellulose membrane. Rat brain mitochondria at different concentrations were used as a positive control. Quality of transfer was assayed by Ponceau staining. The nonspecific binding sites were blocked with 5% (w/v) nonfat milk in mM Tris-Saline buffer pH 8 containing 0.5% Tween 20 (T-TBS). The membranes were incubated at 4° C. overnight with primary antibody (anti sera for bovine complex I 24 kDa/51 kDa, diluted 1:350 in T-TBS containing 2% BSA. The 24 kDa/51 kDa antisera was a gift from Y. Hatefi, Scripps Institute of Research). The blots were washed 3-5 times with T-TBS at room temperature and incubated for 1 hour at room temperature with goat anti-rabbit IgG, diluted 1:10,000 in T-TBS. The blots were then developed with Amersham's ECL and exposed to XLS Kodak film for 20-30 seconds.

Subjects

For protein level of 24 and 5 kDa, samples from 34 schizophrenic patients and 15 control subjects were assayed.

Results

Reference is now made to FIG. 4, which is an ECL western blot analysis of the 24 kDa and 51 kDa subunits of complex I in platelets of schizophrenic patients and healthy control subjects. As shown, protein levels were significantly increased by about 2.5 and 2.0 folds for the 24 kDa and 51 kDa, respectively, in schizophrenic patients at acute relapse as compared to healthy subjects. Rat brain mitochondria were used as positive control.

Example 4

Effect of Dopamine (DA) on Respiration of Cells Through Complex I

Figure 5:
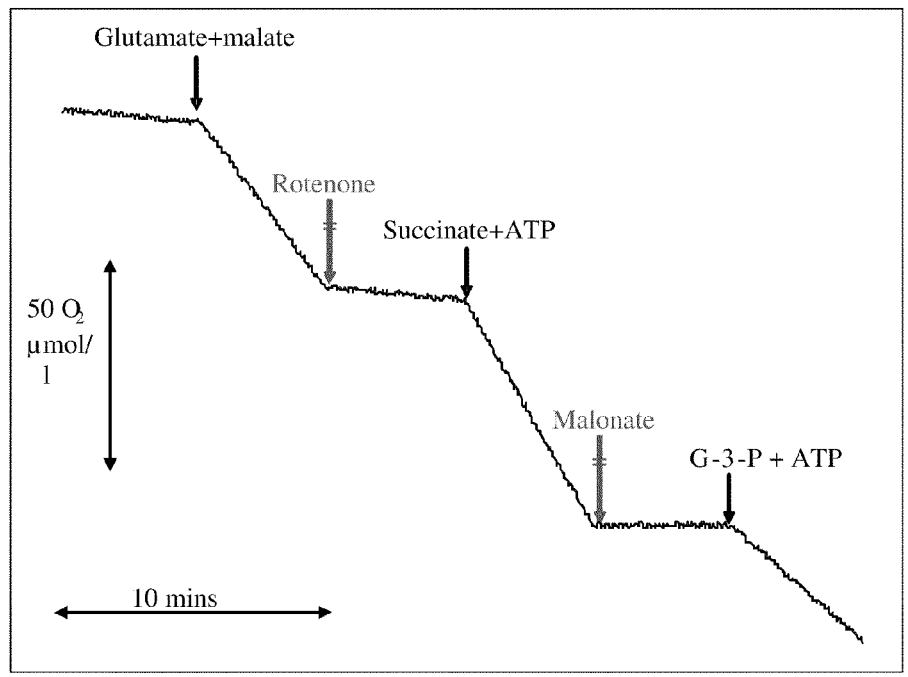
Figure 6:
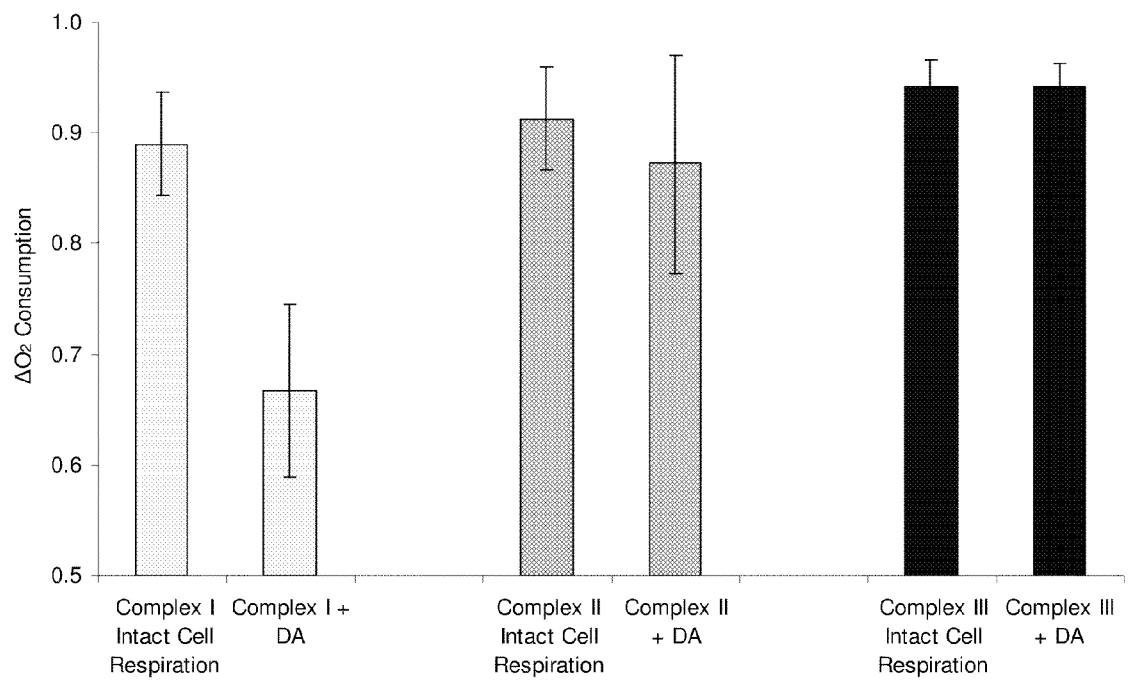
FIG. 6: depicts a representative graph of the respiration rates through different complexes of the respiratory chain.

The effect of dopamine on respiration of cells in intact cells is mediated through the inhibition of complex I. Oxygen consumption through each enzymatic complex of the respiratory chain was measured separately. Respiration rate was determined polarographically using a thermostatically controlled (37° C.) Clark oxygen electrode after 10 minutes of incubation. Respiration rates for each enzyme of the respiratory chain were assessed after the permeabilization of cellular membrane, with 0.001% digitonin followed by the addition of the following substrates and inhibitors: private/glutamate plus malate for complex I induced respiration; succinate, in the presence of rotenone and ATP for complex II induced respiration, and glycerol-3-phosphate, in the presence of rotenone. ATP and malonate (complex II inhibitor) for complex III induced respiration as presented in FIG. 5. Dopamine inhibited respiration through complex I by 33.3±0.07% ($p<0.0006$) but not through complex II and III, further substantiating dopamine's ability to specifically interact with complex I as presented in FIG. 6. Results are means±SD of 3 experiments. The significant differences were analyzed by t-test *$p<0.0006$.

Example 5

Effect of Dopamine (DA) on Respiration of EBV Transformed Lymphocytes in Schizophrenia Isolation of Epstein-Barr Virus (EBV) Trans formed Lymphocytes Lymphocytes were isolated on Ficol and were centrifugated at 270 g for 10 minutes, the cell pellet was infected with 1 ml EBV at 37° C. for 1 h. The sample was then centrifuged at 270 g for 10 minutes to remove the EBV. The infected lymphocytes were-suspended in 5 ml of RPMI 1640 with 20% (v/v) FBS and 1% phytohemagglutinin (PHA) and incubated in a culture flask with culture medium replaced twice a week. Immortalized lymphocytes were then cryopreserved until use in liquid nitrogen.

Figure 7:
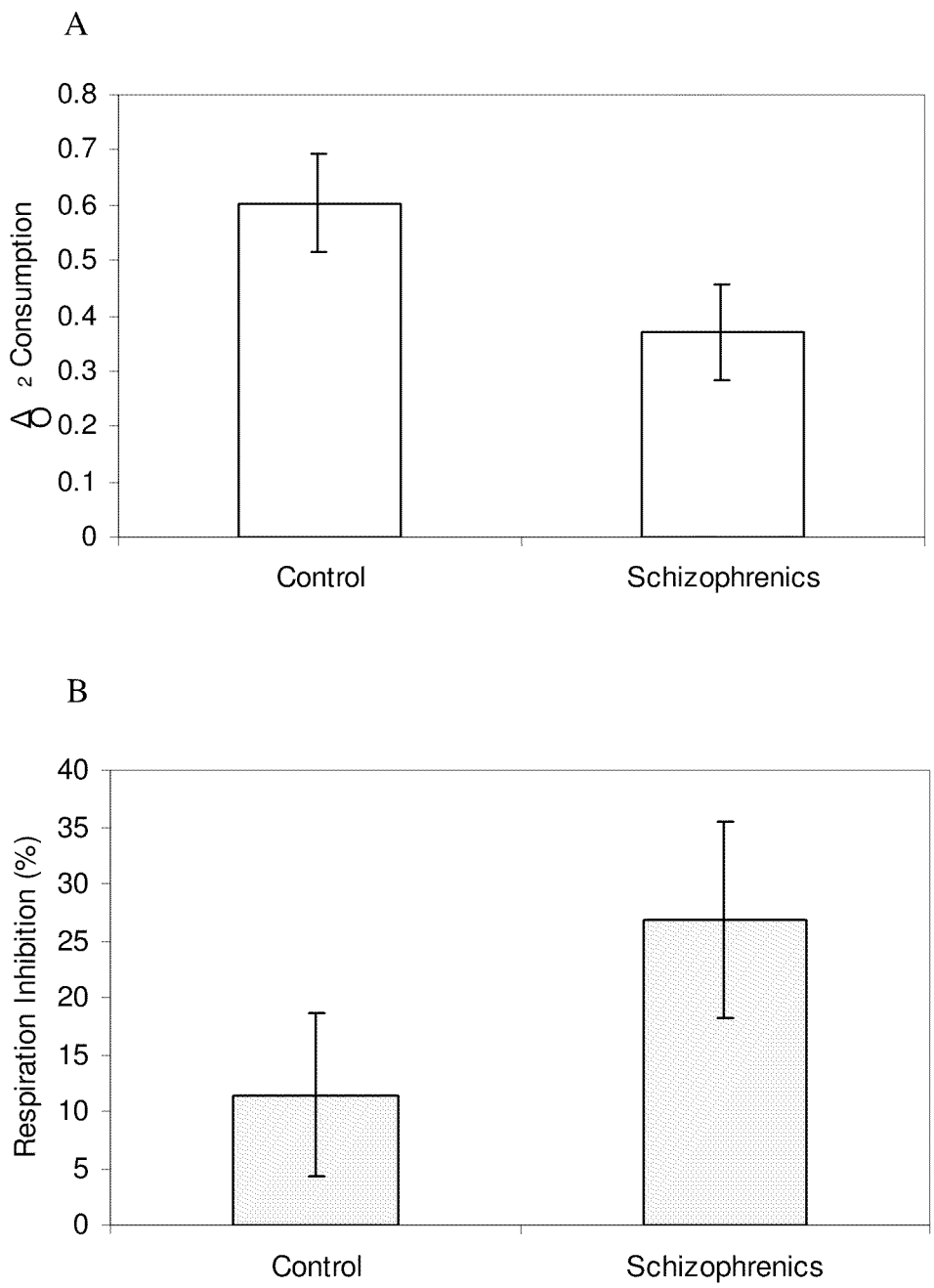
FIG. 7A-B: Basal and dopamine (DA) affected respiration in Epstein-Barr Virus (EBV) transformed lymphocytes derived from schizophrenic patients and healthy subjects. (A) Basal respiration and (B) DA affected respiration in EBV transformed lymphocytes from schizophrenics (n=7) and control subjects (n=7).*p=0.0001 vs. control

Respiration was measured polarographically using a thermostatically controlled (37° C.) Clark oxygen electrode after 10 minutes of incubation. The respiration rates were assessed after the permeabilization of cellular membrane with 0.001% digitonin and the addition of glutamate+malate Results Basal respiration of EBV transformed lymphocytes (lymphoblats) derived from seven schizophrenic patients was significantly lower than that of EBV transformed lymphocytes derived from seven healthy subjects ($0.370 \pm 0.087$ vs. $0.604 \pm 0.089$ $\Delta O_2$ µM/h, $p<0.0001$) as depicted in FIG. 7A. DA induced an inhibition of respiration in both groups but the inhibition was higher by two fold in lymphoblats of schizophrenic patients ($26.8 \pm 8.6\%$) than control subjects ($11.4 \pm 7.2\%$) as depicted in FIG. 7B.

Example 6

Respiration and Antipsychotic Drugs

The effect of antipsychotic drugs on respiration in SH-SY5Y cells was studied. Both typical (haloperidol, chlorpromazine) and atypical antipsychotic drugs (clozapine), but not antidepressant drugs (anafranil, Fluoxetine), specifically inhibit complex I driven mitochondrial respiration as presented in Table 10, and had no effect on respiration through complex IL. Antidepressant drugs also inhibited respiration but not specifically through complex I since the percentage of inhibition was similar to the inhibition through complex II.

TABLE 10

Antipsychotic drugs affect respiration through complex I inhibition

| Drug | % Inhibition - complex I | | % Inhibition - complex II | |
|---|---|---|---|---|
| | $5 \times 10^{-5}$ M | $10^{-4}$ M | $5 \times 10^{-5}$ M | $10^{-4}$ M |
| Haloperidol | $27.2 \pm 4.7^*$ | $47.6 \pm 10.0^*$ | $0.7 \pm 0.7$ | $2.9 \pm 1.8$ |
| Clozapine | $31.2 \pm 5.6^*$ | $39.9 \pm 20.8^*$ | $10.9 \pm 1.6$ | $2.6 \pm 2.4$ |
| Chlorpromazine | $20.9 \pm 18.1^*$ | $43.8 \pm 17.3^*$ | $6.6 \pm 3.5$ | $14.9 \pm 2.1$ |
| Anafranil | $13.0 \pm 11.0$ | $32.1 \pm 8.8^*$ | $11.0 \pm 1.2$ | $22.1 \pm 18.0^{**}$ |
| Fluoxetine | $15.7 \pm 25.5$ | $29.2 \pm 22.7^{**}$ | $15.0 \pm 9.2$ | $25.3 \pm 0.2^*$ |

The significance of inhibition of respiration by the drugs was calculated by student t-test comparing their effects to the basal respiration before they were added.
Values are means ± SD of 4-6 detections.
*p < 0.011,
**p < 0.05

It will be appreciated by persons skilled in the art that the present invention is not limited by what has been described hereinabove and that numerous modifications, all of which fall within the scope of the present invention, exist. Rather the scope of the invention is defined by the claims which follow:

References

Attkisson C, Cook J, Karno M, et al. (1992) Clinical services research. Schizophr. Bull. 18. 561-626.

Barbeau D. Liang JJ, Robitaille Y, Quirion R, Srivastava LK (1995). Decreased expression of yje embrionic form of the neuronal cell adhesion molecule in schizophrenic brains. Proc. Natl. Acad. Sci USA 92, 2785-2789.

Beal MF (1992). Does impairment of energy metabolism result in cytotoxic neuronal death in neurodegenerative illnesses? Ann Neurol. 31, 119-130.

Ben-Shachar D, Zuk R, Gazawi H, Reshef A, Sheinkman A, Klein E (1999) Increased mitochondrial complex I activity in platelets of schizophrenic patients. Inter. J. Neuropsychopharmacol. . 2, 245-253.

Ben-Shachar D, Zuk R, Glinka Y. (1995) Dopamine neurotoxicity: inhibition of mitochondrial respiration. J. Neurochem. 64, 718-723.

Bromet E, Harrow M, Kasl S (1974) Basic principles of epidemiologic research in schizophrenia. In: Handbook of Schizophrenia, vol. 3. Nosology, Epidemiology and Genetics of Schizophrenia. Tsuang MT, Simpson JC eds. Elsevier NY.

Burkhardt C, Kelly JP, Lim YH, Filley CM, Parker WD (1993). Neuroleptic Medications inhibit complex I of the electron transport chain. *Annals of Neurology* 33, 512-517.

Cavalier L, Jazin E, Eriksson I, Prince J, Bave B, Oreland L, Gyllensten U (1995). Decreased cytochrome c oxidase activity and lack of age related accumulation of mtDNA in brain of schizophrenics. Genomics 29, 217-228.

Cohen G, Farooqui R, Kesler N (1997). Parkinson's Disease: A new link between monoamine oxidase and mitochondrial electron flow. Proc.Nat. Acad. Sci. USA 94, 4890-4894.

Da Prada M, Cesura AM, Launany JM, Richards JC (1988). Platelets as a model for neurons? Experientia 44, 115-126.

Davis KL, Kann RS, Ko G, Davidson M (1991). Dopamine in schizophrenia: a review and reconceptualization. American Journal of Psychiatry 148, 1474-1486.

Dingman CW, McGlashan TH (1986) Discriminating characteristics of suicides: Chestnut Lodge follow-up sample including patients with affective disorders, schizophrenia and schizo-affective disorder. Acta. Psychiatr. Scand. 74, 91-97.

Docherty NM, DeRosa M, Andreasen NC, (1996) Communication disturbances in schizophrenia and mania. Arch. Gen. Psychiatry 53, 358-364.

DSM-IV American Psychiatric Association: Diagnostic and Statistical Manual of Mental disorders, 4 th ed (DSM-IV). Washington, DC, APA, 19.

Estornell E, Fato R, Pallotti F, Lenaz G (1993). Assay conditions for the mitochondrial NADH:coenzyme Q oxidoreductase. FEBS 332, 127-131.

Ganguli R, Brar JS, Chengappa KN, Yang ZW, Nimgaonkar VL, Rabin BS (1993) Ann Med. 25, 489-496.

Gavin CE, Gunter KK, Gunter TE (1990). Manganese and calcium efflux kinetics in brain mitochondria, relevance to manganese toxicity. Biochemical Journal 266, 329-334.

Gur RE, Resnick SM, Alavi A, Gur RC, Caroff S, Dann R, Silver FL, Saykin AJ, Chwluk JB, Kudhner M. (1987). Regional brain function in schizophrenia II: repeated evaluation with positron emission tomography. Arch. Gen. Psychiatry 44, 126-129.

Harlow and Lane, Antibodies: A Laboratory Manual, (Cold Spring Harbor Laboratory, Cold Spring Harbor, N.Y.), 1988.

Hatefi Y (1978). Preparation and properties of the enzyme complexes of the mitochondrial oxidative phosphorylation system. *Methods in Enzymology* 53, 3-10.

Hietala J, Syvalahti E. (1996). Dopamine in schizophrenia. Ann Med 28, 557-61.

Kaiya H (1992) Second messenger imbalance hypothesis of schizophrenia. Prostaglandins Leukotriens & Essential Fatty Acids 46, 33-38.

Krige D, Carroll M, Cooper JM, Maesden CD, Schapira AHV (1992). Platelet mitochondrial function in Parkinson's disease. Annals of Neurology 32, 782-788.

Kung L, Roberts RC (1999) Mitochondrial pathology in human schizophrenic striatum: a postmortem ultrastructural stdy. Synapse 31, 67-75.

McComark JG, Denton RM (1989). Influence of calcium ion on mammalian intramitochondrial dehydrogenases. Methods in Enzymology 174, 95-118.

McGlashan TH, (1988) A selective review of recent North American long-term follow-up studies of schizophrenia. Scizophr. Bull. 14, 515-542.

McGlashan TH, Fenton WS (1992) The positive/negative distinction in schizophrenia: review of natural history validators. Arch. Gen. Psychiatry 49, 63-72.

Parker WD, Filley CM, Parks JK (1990). Cytochrome oxidase deficiency in Alzheimer's disease. Neurology 40, 1302-1303.

Prince JA, Blennow K Gottfies CG, Karlsson I Oreland L (1999) Mitochondrial function is differentially altered in the basal ganglia of chronic schizophrenics. Neuropsychopharmacol. 21, 372-379.

Przedborski S, Jackson-Lewis V, Muthane U, Jiang H, Ferreria M, Naini AB, Fahn S (1993). Chronic levodopa administration alters cerebral mitochondrial respiratory chain activity. Ann.Neurol. 34, 715-723.

Raedler TJ, Knable MB, Weinberger DR (1998) Current Opinion in Neurobiol. 8, 157-161.

Ragan CI, Wilson MT, Darley-Usmar VM, Lowe PN (1987). Subfractionation of mitochondria and isolation of the proteins of oxidative phosphorylation. In: Darely-Usmar, V.M., Rickwood, D. and Wilson, M. (Eds.), Mitochondria, a Practical Approach (pp. 79-112). London: IRL Press.

Rosental RE, Hamud F, Fiskum G, Vrghese PJ, Sharpe S (1987) Cerebral ischemia and reperfusion: prevention of brain mitochondrial injury by lidoflazine. J. Cereb. Blood Flow Metab. 7, 752-758.

Schapira AHV, Cooper JM, Dexter D (1990). Mitochondrial complex I deficiency in Parkinson's disease. J. Neurochem. 54, 823-827.

Schroder Holcomb HH, Cascella NG, Thaker GK, Medoff DR, Dannals RF, Tamminga CA (1996). Functional sites of neuroleptic drug action in the human brain: PET/FDG studies with and without haloperidol. Am. J. Psychiatry 153, 41-49.

Seeman P. (1987) Dopamine receptors and the dopamine hypothesis of schizophrenia. Synapse 1,133-152.

Sheitman BB., Lee H., Strauss R. Lieberman JA. (1997) The evaluation and treatment of first-episode psychosis. Schizophrenia Bull 23, 653-61.

Singer TP (1974). Determination of the activity of succinate, NADH, Choline and glycerophosphate dehydrogenases. In: Glick, E. (Ed.), Methods of Biochemical Analysis. Vol. 22 (pp. 123-175). New York: International Science.

Storrie B, Madden EA (1990). Isolation of subcellular organelles. Methods in Enzymol. 182, 203-225.

Strunecka A., Ripova D, (1999) What can the investigation of phosphoinositide signaling system in platelets of schizophrenic patients tell us? Prostaglandins Leukotriens & Essential Fatty Acids 61, 1-5.

Takahashi Y (1954). An enzymological study on brain tissue of schizophrenic patients. Carbohydrate metabolism. Folia Psychiatrica Neurologica Japonica 7, 214-237.

Tamminga CA, Thaker GK, Buchanan R, Kirkpatrick B, Alphs LD, Chase TN, Carpenter WT (1992). Limbic system abnormalities identified in schizophrenia using positron emission tomography with fluorodeoxyglucose and neocortical alterations with deficit syndrome. Arch. Gen. Psychiatry 49, 522-530.

Tsuang MT, (1978) Suicide in schizophrenics, manics, depressives and surgical controls: a comparison with general population suicide mortaliy. Arch. Gen Psychiatry 35, 153-155.

Uranova NA, Aganova EA (1989). Ultrastructure of synapses of the anterior limbic cortex in schizophrenia. Zhurnal Nevropatologii I Psikhiatrii Imeni S-S- Korsakova. 89, 56-59.

Whatley SA, Curi D, Das Gupta F, Ferrier IN, Jones S, Taylor C, Marchbanks RM (1998). Superoxide, neuroleptics and the ubiquinone and cytochrome b5 reductases in brain and lymphocytes from normals and schizophrenic patients. Mol. Psychiatry 3, 227-237.

Whatley SA, Curi D, Marchbanks RM (1996). Mitochondrial involvement in schizophrenia and other functional psychoses. Neuroch. Res. 21, 995-1004.

Willner P (1997) The dopamine hypothesis of schizophrenia: current status, future prospects. Int Clin Psychopharmacol 12, 297-308.

Wirz-Justce A (1988). Platelet research in psychiatry. Experientia 44, 152-155.

Wyatt RJ, Henter I, Leary MC, Taylor E (1995) An economic evaluation of schizoprenia-1991. Soc. Psychiatry Psychiatr. Epidemiol. 30, 196-205.

Yao JK, van Kammen DP (1996) Incoporation of 3H-arachidonic acid into platlet phospholipids of patients with schizophrenia Prostaglandins Leukotriens & Essential Fatty Acids 55,21-26.

What is claimed is:

1. A method for diagnosing schizophrenia in a subject, the method comprising the steps of:
   a. obtaining a blood sample from said subject;
   b. isolating lymphocytes from said blood sample;
   c. infecting said lymphocytes with Epstein Ban Virus (EBV);
   d. determining the cellular basal respiration through mitochondrial complex I enzyme in said EBV-transformed lymphocytes;
   e. adding an inhibitor of cellular respiration to the EBV-transformed lymphocytes;
   f. determining the percent (%) inhibition of said cellular basal respiration through complex I in said EBV-transformed lymphocytes in the presence of said inhibitor; and
   g. comparing said percent (%) inhibition of said EBV-transformed lymphocytes from said subject with the percent (%) inhibition of the cellular basal respiration through complex I in the presence of said inhibitor in EBV-transformed lymphocytes from a nonnative person, wherein a higher percent (%) inhibition of cellular respiration through complex I enzyme in said EBV-transformed lymphocytes from said subject as compared to the percent (%) inhibition in EBV-transformed lymphocytes from said normative person is indicative of schizophrenia in said subject.

2. The method of claim 1, wherein said higher percent (%) inhibition of said cellular respiration through complex I enzyme in said EBV-transformed lymphocytes from said subject, is higher by at least twofold, in the range of between 2-6 fold higher as compared to EBV-transformed lymphocytes from said normative person.

3. The method of claim 1, wherein said inhibitor is a catechol.

4. The method of claim 3, wherein said catechol is L-DOPA, dopamine or norepinephrine (NE).

5. A method for diagnosing schizophrenia in a subject, the method comprising the steps of:

a. obtaining a blood sample from said subject;
b. isolating lymphocytes from said blood sample;
c. infecting said lymphocytes with Epstein Barr Virus (EBV);
d. determining the cellular basal respiration through mitochondrial complex I enzyme in said EBV-transformed lymphocytes;
wherein a decrease in cellular basal respiration through complex I in said subject as compared to cellular basal respiration through complex I in a normative person is indicative of schizophrenia in said subject.

6. The method of claim 1, wherein the cellular basal respiration of said normative person is between 0.5-0.7 μM/h.

7. The method of claim 1, wherein the percent (%) inhibition of cellular respiration of said normative person is between 4%-20%.

8. The method of claim 1, wherein said inhibitor of cellular respiration is dopamine.

9. The method of claim 1, wherein said step of determining the cellular basal respiration through mitochondrial complex I enzyme comprises: permeabilizing the cellular membrane with digitonin; adding glutamate and malate; and polarographically measuring respiration using a thermostatically controlled Clark oxygen electrode.

10. The method of claim 5, wherein said decrease in cellular basal respiration through complex I enzyme in lymphocytes from said subject is between 20-40% as compared to a normative person.

11. The method of claim 5, wherein said cellular basal respiration through complex I in lymphocytes from said subject is approximately 66% of the cellular basal respiration through complex I in lymphocytes from said normative person.

12. The method of claim 5, wherein the cellular basal respiration of said normative person is between 0.5-0.7 μM/h.

13. The method of claim 5, wherein said step of determining the cellular basal respiration through mitochondrial complex I enzyme comprises: permeabilizing the cellular membrane with digitonin; adding glutamate and malate; and polarographically measuring respiration using a thermostatically controlled Clark oxygen electrode.

* * * * *